United States Patent [19]

Nakada

[11] Patent Number: 5,723,496

[45] Date of Patent: Mar. 3, 1998

[54] METHOD FOR PREVENTION AND TREATMENT OF HARMFUL EFFECTS OF INTRACELLULAR ACIDOSIS

[75] Inventor: Tsutomu Nakada, San Francisco, Calif.

[73] Assignee: The Regents of University of California, Oakland, Calif.

[21] Appl. No.: 404,938

[22] Filed: Mar. 15, 1995

Related U.S. Application Data

[63] Continuation of Ser. No. 142,194, Oct. 22, 1993, abandoned, which is a continuation-in-part of Ser. No. 664,933, Mar. 5, 1991, Pat. No. 5,312,839.

[51] Int. Cl.⁶ .................................................. A61K 37/52
[52] U.S. Cl. ........................ 514/634; 514/634; 514/665; 514/558; 514/238.8; 514/231.2
[58] Field of Search ................................ 514/634, 665, 514/558, 238.8, 231.2

[56] References Cited

PUBLICATIONS

Gregorios Papastoitsis, et al., Identification of a Metalloprotease from Alzheimer's Disease Brain Able to Degrade the β-Amyloid Precursor Protein and Generate Amyloidogenic Fragments, *American Chemical Society, Biochemistry*, 33:192–199 (1994).

Frank Ashall, et al., Role of the β-amyloid precursor protein in Alzheimer's disease, *TIBS* 19:42–45 (Jan. 1994).

Eric Growing, et al., Chemical Characterization of Aβ 17–42 Peptide, a Component of Diffuse Amyloid Deposits of Alzheimer Disease, *The Journal Of Biological Chemistry*, vol. 269, No. 15, pp. 10987–10990 (Apr. 15, 1994).

Evelyne Terzi, et al., Reversible Random Coil–β–Sheet Transition of the Alzheimer β–Amyloid Fragment, *Biochemistry*, 33:1345–1350, (1994).

Debra Burdick, et al., Assembly and Aggregation Properties of Synthetic Alzheimer's A4/β Amyloid Peptide Analogs, *The Journal of Biological Chemistry*, vol. 267, No. 1, pp. 546–554, (Jan. 5, 1992).

Colin J. Barrow, et al., Solution Structures of β Peptide and Its Constituent Fragments: Relation to Amyloid Deposition, *Science*, 253:179–181 (1991).

*Primary Examiner*—Marianne M. Cintins
*Assistant Examiner*—Keith MacMillan
*Attorney, Agent, or Firm*—Hana Verny

[57] ABSTRACT

Compounds and a method useful for protection of tissue cells in a mammalian body from irreversible damages due to lactic acidosis caused by oxygen deficiency. The protection is achieved by administering a compound having a cell membrane permeability and/or ability to cross the blood brain barrier, said compound being able to provide a buffering action to prevent an increase in a hydrogen ion concentration over the physiologically acceptable levels or able to shift the intracellular pH to a more desired alkaline level.

9 Claims, 9 Drawing Sheets

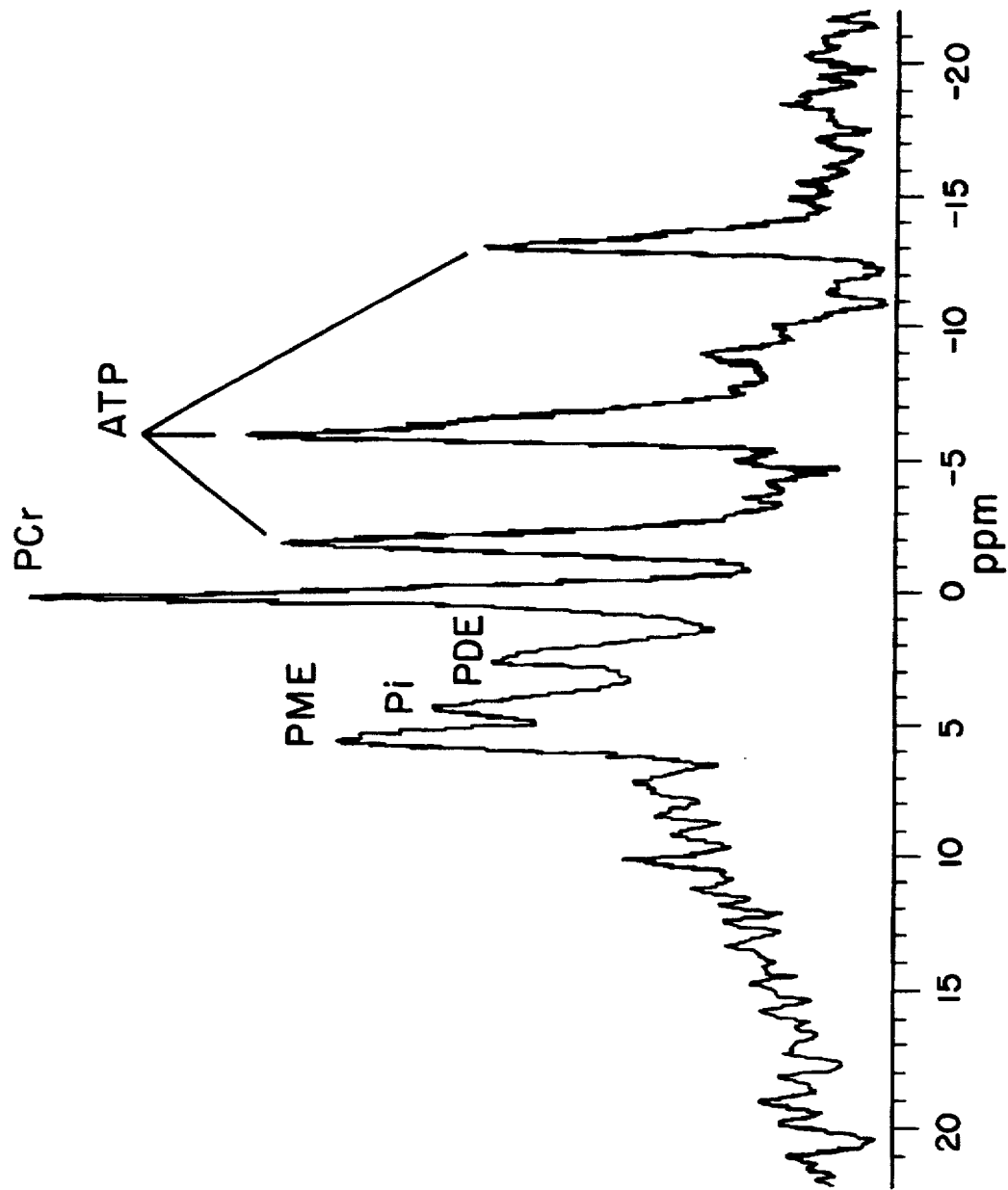

METHOD FOR PREVENTION AND TREATMENT OF HARMFUL EFFECTS OF INTRACELLULAR ACIDOSIS

This is a continuation of application U.S. Ser. No. 08/142,194 filed on Oct. 22, 1993, now abandoned which is a continuation-in-part of Ser. No. 07/664,933, now U.S. Pat. No. 5,312,839, filed Mar. 5, 1991.

The present invention was made in the course of research supported by research grants GM 37197, RR 02511 from the National Institute of Health. The United States Government may have certain rights in this invention.

BACKGROUND OF INVENTION

1. Field of Invention

The present invention relates to a method for prevention and treatment of harmful effect of intracellular acidosis. The method protects cells and tissues from irreversible injury due to lactic acidosis. More specifically, this invention relates to method for administering compounds that are permeable through the blood-brain-barrier or through the cell membrane and provide a higher buffering capacity against an increase in intracellular hydrogen ion concentration or, alternatively, shift intracellular pH to a more alkaline value. The invention also relates to a method for protection of tissues and cells in mammals, including humans, from the irreversible damages due to lactic acidosis caused by the accumulation of lactic acid in the cells under the condition of oxygen deficiency such as anoxia, hypoxia, hypothermia or ischemia. Finally, the method is useful for treatment of Alzheimer disease.

2. Background Art and Related Art Disclosures

Cellular hypoxia or anoxia represents one of the fundamental sequelae of compromise in the microcirculation. In the brain, which is heavily dependent on glucose as an energy source, cellular hypoxia or anoxia results not only in a reduction in energy production but also in lower pH, leading to tissue acidosis.

Several lines of evidence now support the concept that lactic acidosis plays a key role in determining the outcome of brain anoxia/ischemia. Since it appears that acidosis is more harmful to brain than the lactate molecule per se, any condition which lessens brain acidosis associated with anoxia/ischemia should confer cytoprotective effects on brain tissue against anoxic/ischemic insults. Theoretically, there are three categorical conditions capable of preventing severe brain acidosis, namely, the conditions which: (1) limit lactic acid production; (2) permit a higher acid buffering capacity against lactic acid; or (3) shift baseline brain pH towards the alkaline side. Indeed, previous studies demonstrated favorable effects of all three categories on the outcome of brain anoxia/ischemia.

Recent findings show that in addition to maintenance of ATP above critical cellular levels, preservation of normal pH in the presence of excess protons is of fundamental importance to cell survival.

Cells, particularly cells of the central nervous system, also called neuronal cells, neurons, or cerebral cells, are heavily dependent on glucose as an energy source. When neuronal cells are placed under the condition of oxygen deficiency such as anoxia, hypoxia or ischemia, the normal oxidative metabolism is inhibited and substituted with anaerobic glycolysis. The glycolytic pathway for production of glucose in the absence of oxygen is not only uneconomical but it also produces lactic acid. As the result of anaerobic glycolysis, lactic acid is accumulated in neuronal or other cells resulting in lactic acidosis. If the lactic acidosis is permitted to develop and persist for certain time in cells, those cells are irreversibly injured and damaged. This is known as the "Lactate Hypothesis" described for example in *Neurology*, 33:229 (1983); *Stroke*, 11:355 (1980); *J. Neurochem.*, 52: 154 (1989).

Lactic acidosis was shown to play a key role in determining the outcome of brain anoxia or ischemia. Conditions which permit higher glucose supplies to anoxic or ischemic brain tissue such as systemic hyperglycemia, complete anoxia, or partial ischemia, consistently result in higher levels of lactate, an unfavorable condition for cell survival (*Arch. Neurol.*, 34:65 (1977)). In contrast, conditions such as fasting, which limit lactate production, can prevent reactive hyperglycemia during anoxia or partial ischemia and provide a favorable outcome. Since it appears that the acidosis is more harmful to brain cells than the lactate molecule per se, theoretically, conditions which permit higher acid buffering capacity or shift intracellular pH to a more alkaline value should also protect brain against anoxic or ischemic insults. This invention concerns compounds having such capability and method for protection of brain and other cells from anoxic injury.

For protection of the central nervous system and other cells in mammals from irreversible injury caused by oxygen deficiency, compounds such as calcium antagonists, e.g. flunarizine or dextromethophan, and free radical scavengers such as barbitals were previously used. Calcium antagonists are intended to prevent the influx of calcium ions into the neuronal cells due to exhaustion of energy, while free radical scavengers are used to prevent cell damage caused by active oxygen produced by the free radical capturing mechanism connected with glycolysis to provide energy. Thus, the currently used conventional drugs are directed only to treatment of the phenomena caused by the cessation of the energy supply in cerebral cells.

On the other hand, tromethamine having a chemical formula 2-amino-2-hydroxymethyl-1,3-propanedil is a known drug for treatment of acidosis. This drug reacts with carbonate ion present in blood circulation and in this way it enhances the bicarbonate ion concentration. It is not intended to neutralize hydrogen ion in cells directly. Sodium bicarbonate is similarly usable in cells to prevent acidosis by neutralizing hydrogen ion and to retain a normal bicarbonate ion concentration in blood. Thus, conventional drugs for acidosis treatment are all concerned with the control of a carbonate buffering system.

Since the excessive formation of hydrogen ion causes the change in intracellular pH, it would be highly advantageous to have available a drug or mechanism to maintain the normal intracellular physiological pH. It would similarly be advantageous to have available a drug that is able to shift intracellular pH to a more alkaline level, thereby reducing the deleterious deposition of beta-amyloid fibers that are believed to be a factor in promoting Alzheimer's disease.

It has recently been discovered and described, for example, in *Neurology*, 40 (Supp. 1), 281 (1990), that immediately after birth the cerebral cells of newborn mammals are highly resistant to oxygen deficiency. For instance, newborn rats were shown to survive for up to 12 minutes even in such extreme conditions as when being placed under a pure nitrogen atmosphere.

These findings suggest some additional mechanism possessed by newborns by which they can counter the insufficient supply of oxygen and prevent the cells, primarily the central nervous system cells, from irreversible injury and damage caused by cellular hypoxia or anoxia. If such substance and/or system is present in newborns and such compound or the components of such system could be identified and utilized for the adults, it could effectively prevent and/or protect against the development of irreversible change in the cells caused by metabolic acidosis, anoxia, hypoxia or ischemia. Such compounds and/or system would have to be non-toxic, physiologically acceptable, permeable through the cell membrane, be able to cross the blood-brain barrier and prevent an increase in hydrogen ion concentration by either buffering the increase in free hydrogen ions or alternatively shifting intracellular pH to a more alkaline level, e.g. act as an alkaline shifter.

Guanidinoethane sulfate (GES) is a taurine analogue originally described in *J. Pharmacol. Ext. Therap.*, 211:465 (1979), as competitive inhibitor of taurine transport into the brain. Recent studies demonstrated that GES is an effective alkali shift agent of intracellular brain pH. (*Soc. Neurosci.*, 21 Annual Meeting, Abstract, 1078, Oct. 5, 1992). Entry of GES across the blood-brain barrier (BBB) is likely to be in the uncharged form. Following free diffusion into the cytosol, the ratio between uncharged and charged forms will equilibrate according to cytosolic pH and the pKa value of GES. Due to the high pKa value (18.48) of its guanidino moiety, virtually all GES in brain cytosol is in the charged form. Therefore, replacement of intracellular taurine (⅛ of which remains in the uncharged form) by GES results in a shift of brain pH towards a higher value. GES possesses this unique property as alkali shift agent.

The precise role of acidosis in delayed neuronal death in the CA1 region of the hippocampus remains to be elucidated. Studies described in *Stroke*, 18:412 (1987) demonstrated that post-ischemic acidosis is more pronounced in the CA1 region and, hence, acidosis may play a role in the observed selective vulnerability of the CA1 region towards ischemia. It is apparent that acidosis is not the direct cause of delayed neuronal death. However, acidosis may play a role as trigger of deleterious biochemical/biophysical cascades which lead to delayed neuronal death. Accordingly, current invention concerns the protective effects of alkali shift brought about by GES on delayed neuronal death of CA1 neurons using the gerbil forebrain ischemia model.

It is therefore a primary object of this invention to provide a method for prevention and treatment of harmful effect of intracellular acidosis by administering compounds which are permeable through the cell membrane in tissue cells or are able to pass the blood-brain barrier and enter the brain cells. These compounds prevent an increase in intracellular hydrogen ion concentration either by acting as an alkaline shifter or by buffering the increase in hydrogen ion. Administration of these compounds is effective in protection of irreversible injury of said cells due to lactic acidosis caused by oxygen deficiency.

All references cited in the application are hereby incorporated by reference in their entirety.

SUMMARY

A primary aspect of this invention is a protection of the brain or other cells or tissues from the damage caused by the intracellular acidosis due to ischemia, hypothermia or due to other metabolic, biochemical or biophysical causes by providing a compound effecting alkali shift.

Another aspect of this invention is a method for protection of brain or other cells and tissues from the irreversible damages due to lactic acidosis caused by the accumulation of lactic acid in the tissues and cells under the condition of oxygen deficiency, which method comprises administering to a mammal a non-toxic substance having pKa between 6.8 and about 11.4 for which the cell membrane is permeable, which is able to cross the blood-brain barrier and which prevents an increase in hydrogen ion concentration by either exerting a buffering action in the cells and tissues or alternatively shifting the intracellular pH to a more desirable alkaline value.

Another aspect of this invention are compounds useful for protection of tissues and cells from the irreversible injury due to the over production of the free hydrogen ions, which compounds are permeable through the cell membrane and act as a buffering agent to prevent and neutralize an increase of hydrogen ion due to an insufficient supply or availability of oxygen or alternatively act as an agent that promotes shifting of intracellular pH to a more alkaline level.

Still another aspect of this invention is a method for protection of cells from harmful effects of intracellular acidosis by administering compounds which cross the blood-brain barrier, which are cell membrane permeable, which possess a buffering action against increase of the hydrogen ion or effect the alkali shift, which have preferably pKa of no less than 6.8, which behave as hydrogen ion acceptor and which are chosen from the group of heterocyclic compounds, either monocyclic or polycyclic, having nitrogen as the only hetero atom and wherein a functional group, selected from the class including —NH$_2$, =NH, ≡N, or =C=N—, is bound to said heterocyclic compound directly or through an alkyl group.

Still another aspect of this invention is a method where the buffering compounds are morpholino compounds that cross the blood-brain barrier or are cell membrane permeable wherein the functional group of morpholino compound bound to the hetero nitrogen atom or alkyl group is NH$_2$; =NH; ≡N or =C=N—.

Still another aspect of this invention is a method for protection of cells and tissues against anoxic injuries by providing a patient facing or encountering oxygen deficiency, the compound of the buffering or alkaline shifting system of the current invention to combat the metabolic acidosis caused by oxygen deficiency and/or prevent its development.

Final aspect of this invention is prevention and treatment of Alzheimer disease by administering compounds which cross the blood-brain barrier, which are cell membrane permeable, which possess a buffering action against increase of the hydrogen ion or effect the alkali shift, which have preferably pKa of no less than 6.8 and no higher than 11.4, which behave as hydrogen ion acceptor and which are chosen from the group of heterocyclic compounds, either monocyclic or polycyclic, having nitrogen as the only hetero atom and wherein a functional group, selected from the class including —NH$_2$, =NH, ≡N, or =C=N—, is bound to said heterocyclic compound directly or through an alkyl group.

BRIEF DESCRIPTION OF DRAWINGS

FIG. 9 represents $^{31}P$ spectra of gerbil brain used in pH determinations.

DETAILED DESCRIPTION OF THE INVENTION

Figure 1:
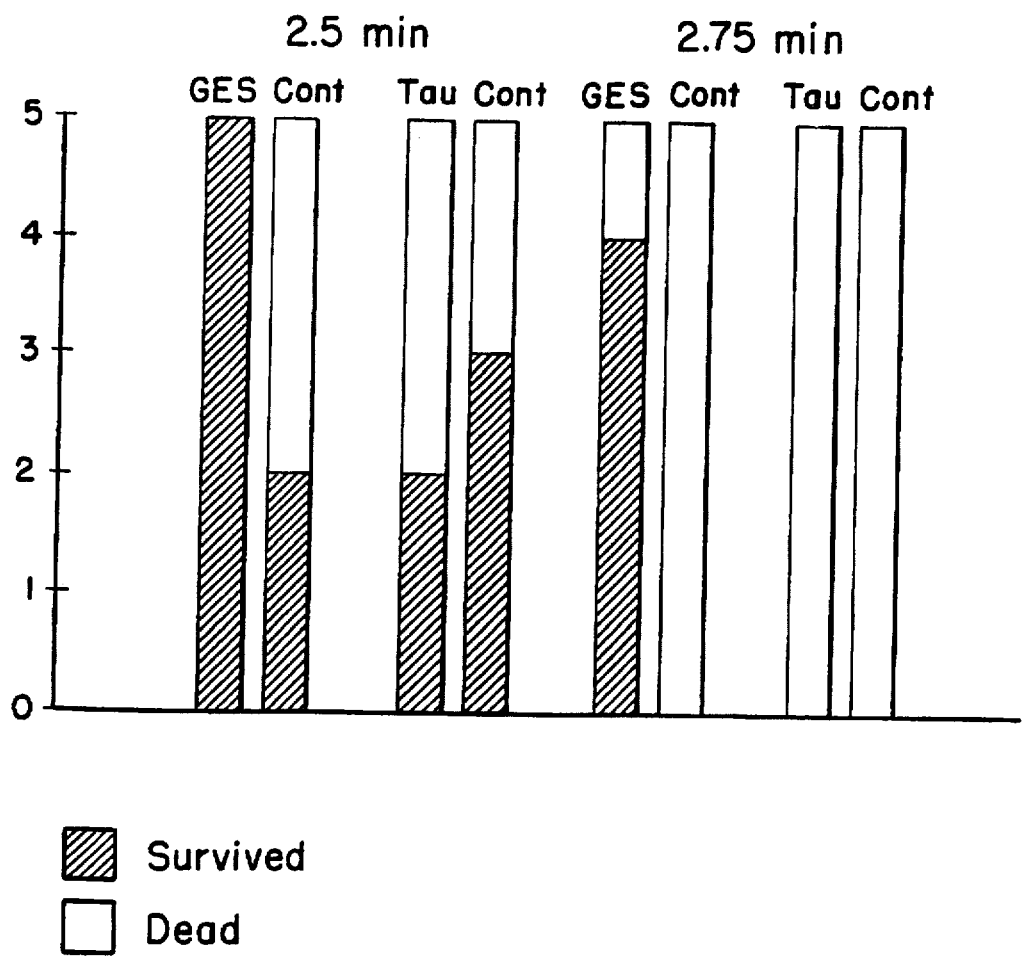
FIG. 1 illustrates the survival rate of adult mice exposed to anoxia pretreated with guanidinoethane sulfate or taurine compared to controls treated with saline.

This invention concerns and provides compounds and a method for prevention and treatment of harmful effect of intracellular acidosis. The method protects cells, particularly central nervous system cells, from the irreversible injury caused by the deficiency of oxygen or by the overproduction of hydrogen ions. Both these events cause the metabolic, particularly lactate acidosis, changes in tissue and cell pH, and ultimately result in irreversible injury and/or death of cells. The method for prevention and treatment of intracellular acidosis is effected by administration of compounds able to shift intracellular pH toward alkaline pH.

Compounds of this invention must have the following characteristics. They must be able to cross the blood-brain barrier, be cell membrane permeable, possess a buffering action against increase of the hydrogen ion or effect the alkali shift, have preferably pKa of no less than 6.8 and no higher then 8.4, behave as hydrogen ion acceptor. These compounds are preferably chosen from the group of heterocyclic compounds, either monocyclic or polycyclic, having nitrogen as the only hetero atom wherein a functional group, selected from the class including $-NH_2$, $=NH$, $=N$, or $=C=N-$, is bound to said heterocyclic compound directly or through an alkyl group. However, other compounds listed below are also intended to be within the scope of this invention. These compounds must be able to provide an additional buffering system that effectively counters a metabolic acidosis, maintains a stable pH in tissues and cells and in this way protects tissue homeostasis. Alternatively, compounds of this invention protect cells by shifting intracellular pH to alkaline, thereby reducing the deleterious effect of increased hydrogen concentration that accompanies metabolic acidosis.

The discovery of this invention is based on and is an extension of the primary homeostatic requirement for the constancy and the regulation of the internal bodily environment of which an indivisible part is a cellular stability and ions and ionic balance. Bodily internal ionic balance is maintained by buffer systems which efficiently accommodate the addition or formation of moderate amounts of acid or base without a marked change in the hydrogen ion concentration.

In adult individuals, homeostasis or the equilibrium of the hydrogen ion concentration is maintained by the extremely sensitive buffering system comprising a combination of carbonate and non-carbonate buffer system. The combination buffer system contains carbonate, bicarbonate, phosphate, sulfate and protein buffers. The results of NMR measurement obtained and described below suggests, however, the presence of a third buffering system in newborn individuals. This system somehow neutralizes the hydrogen ion produced by the dissociation of the lactic acid accumulated under the condition of oxygen deficiency and allows maintenance of the constant pH in central nervous system cells around pH 7.24.

Such a system requires an equilibrium mixture of ions and undissociated molecules which will resist any attempt to disturb the intracellular pH and will be able to maintain it at physiological levels.

The cellular pH at 7.24 represents physiologically optimal conditions and pH 6.8 represents the absolute low limit to the physiologically acceptable conditions. When the pH level drops around or below this point, the survival of cells becomes extremely difficult.

The survival of cells depends not only on the low pH levels but also on the length of time the cells are submitted to such low pH levels. Thus, for example, a momentary drop of pH to 6.8 would probably not result in permanent injury to cells if it would be immediately neutralized by buffering action and pH would be brought to the physiologically acceptable levels. This would also be achieved if there was a shift in intracellular pH to a more alkaline level to offset the decrease in pH that accompanies oxygen deficiency. On the other hand, the extended time exposure to pH around 6.8–7.0 would probably result in irreparable injury to cells and tissues. It is therefore important that an effective buffering or alkaline shifting system be available to treat patients that have had a drop in intracellular pH below 7.24 and particularly drops to levels around 6.8.

The most efficient buffering action of a compound is expected within a range of the pH value being nearly equal to its pKa value. Thus, the new buffering compound should have a pKa value of not less than 6.8, but preferably higher, or the buffering system containing such compound should be a combination of compounds of which the cumulative pKa is at least 6.8.

The new compound and/or new buffering system will have to work according to the principle of a buffer solution, illustrated as follows:

A weak acid (HA) in solution partially dissociates into proton and its conjugate base ($A^-$). Such a solution has the buffering capacity, i.e., the ability to resist pH changes when a base or acid is added to it. If a strong acid is added to the buffer solution, the hydrogen ions are picked up by the conjugate base of the buffer according to equation:

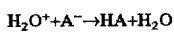

If a strong base is added to the buffer solution, the hydroxyl ions are picked by the weak acid of the buffer, according to the equation:

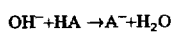

The solution is most efficient as a buffer when it contains equal amounts of a weak acid (HA) and its conjugate base ($A^-$).

According to the Henderson-Hasselbalch equation, the pH of the buffering system depends on the compound's pKa and thus $$pH = pKa + \log(A^-/HA)$$

When HA equals A, log (A⁻/HA) equals zero. Therefore, a buffer solution has optimal buffering capacity at pH=pKa.

The illustration of one buffer system which is present in the body and is connected with and responsible for the disposition of an excess of hydrogen ions formed during metabolic acidosis is a carbonate buffer. The carbonate buffer system represents the main buffer system for mammals. At physiological pH, i.e., at pH=7.4, carbonate ($CO_3^{2-}$) levels are negligible and, therefore, cytosolic carbonate is either in the form of carbonic acid ($H_2CO_3$) or bicarbonate ($HCO^-_3$). Titration studies have shown the pKa value of physiological carbonic acid/bicarbonate solution with $pCO_2$ of 40 mmHg at 37° C. to be 6.12.

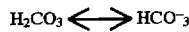

pKa=6.12

Therefore, it is apparent that carbonate itself is not an optimal buffer at physiological pH.

Despite its less than optimal pKa value to buffer at physiological pH, the carbonate system has one critical advantage for biological systems, namely, a rapid adjustment of carbonic acid levels by manipulation of $pCO_2$. Metabolic acidosis brought about by excess acid formation is known to be quickly compensated by a decrease in $pCO_2$ by hyperventilation. This rapid control by respiration is a notably very efficient and accurate system for acid-base control. This mechanism is well-developed in normal healthy adult mammals but is not usable for fetus and is underdeveloped in newborn mammals. Thus, it is logical that both a fetus and newborns possess some other mechanism how to prevent tissue acidosis.

Attempts to measure and compare the lactate ion concentration and the hydrogen ion concentration in the central nervous system cells of newborn rats and mature rats placed under the condition of oxygen deficiency, using nuclear magnetic resonance (NMR) spectroscopy, revealed that there is no significant difference with regard to the increase of the lactate ion concentration between newborn rats and adult rats. Thus, the higher concentration of lactose were observed in both newborns and adult animals following the anoxic exposure. However, a significant difference was produced when the hydrogen ion concentration was measured. Namely, it was found that the hydrogen ion concentration in adult rats was increased in proportion to the increase of the lactate ion concentration, while the hydrogen ion concentration in newborn rats increased only slightly with the increase of the lactate ion concentration. Thus, there was dependence of the hydrogen/lactose ion concentration in adult animals while no such dependence was observed in newborn animals. This observation suggests the presence of some additional or different mechanism which prevents development of acidosis in newborns.

One of the most dramatic alterations in the mammal associated with birth is the change in lung function. During fetal life, $pO_2$ and $pCO_2$ homeostasis are totally dependent on the mother. Following birth, these come under the newborn's own control. While $O_2$ is an essential substrate for biological energy production in oxidative phosphorylation, $CO_2$ plays a fundamental role in acid-base balance as a part of the carbonic acid/bicarbonate buffer system. Hemoglobin, the blood oxygen delivery system, is present in the fetus in an unique type called fetal hemoglobin. Fetal hemoglobin undergoes dramatic adaptational changes after birth to the adult type normal hemoglobin. It would therefore not be surprising if the acid-base regulatory system would similarly possess a specific system during fetal life which undergoes adaptational changes to the adult type system after birth.

In view of the above findings that the newborn mammals possess a certain mechanism to prevent damage due to oxygen deficiency, the search for any substance present in newborn cerebral cells which may be present in extraordinary quantities in newborns or which is not present in adults, was initiated. Such substance would have to be present in neuronal cells during the fetal period in a considerable amount, should be able to cross the blood-brain barrier but should decrease rapidly after birth.

As the result of such research, it is now believed that an amino acid taurine is such a substance. Taurine seems to be present in high amounts in newborn animals but in much smaller amounts in adult animals. It does cross the blood-brain barrier in newborns but it has no such effect in the adults. It possesses excellent buffering properties. Therefore, conceivably, taurine could be a key substance forming said third buffer system present in fetus or in newborn mammals.

When quantitatively measured, it has been discovered that taurine is present in the cerebral cells of newborn rats immediately after birth in the relatively high levels of about 18 mM and is subsequently decreased to a low level of about 4 mM within about one month after birth. At that time, taurine is replaced by N-acetylaspartic acid (NAA) for the maintenance of the osmotic pressure and ionic balance in cerebral cells which was previously, before and early after birth, maintained by taurine containing buffer.

Taurine (2-amineethanesulfonic acid) of formula $NH_2CH_2CH_2SO_3H$ is a primary amine containing compound having pKa value 8.74 which compound exhibits a buffering action against the increase of the hydrogen ion concentration under the physiological conditions. To the contrary, N-acetylaspartic acid is a dicarboxylic acid which does not show a buffering capacity with regard to the increase of the hydrogen ion concentration. Levels of taurine and NAA were studied with respect to their changes dependent on the time after birth of the animal.

Relative taurine and NAA levels were assessed using high resolution proton spectroscopy of brain perchloric acid (PCA) extracts. One and 10 days old pups were sacrificed immediately after completion of the study by exsanguination under pentobarbital anesthesia. Brains were removed and fixed in liquid nitrogen. The frozen brains were pulverized in a liquid nitrogen cooled mortar and pestle and mixed with powdered frozen PCA, 0.5N, 4 volumes. The powder mixture was centrifuged in liquid nitrogen cooled centrifuge tubes at 16,000 r/min at −4° C. for 30 minutes.

Figure 6:
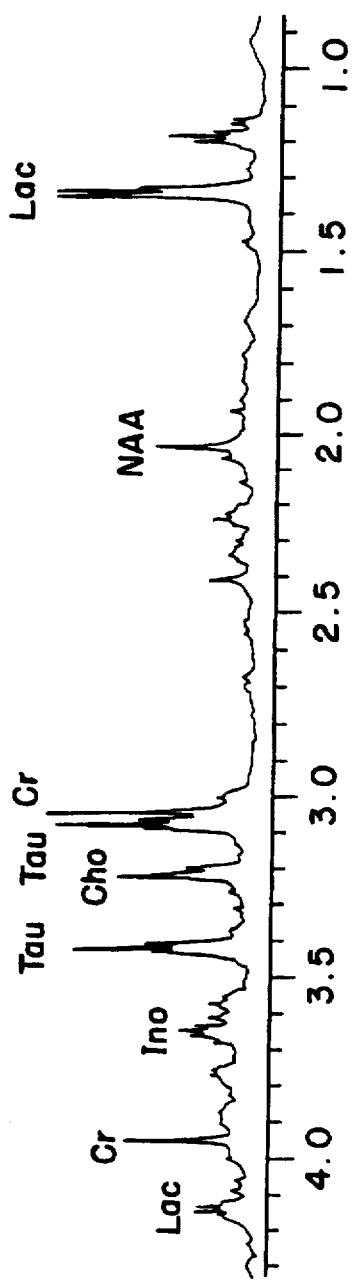
FIG. 6 is a representative high resolution proton spectrum of PCA extract of pup brains.
Figure 7:
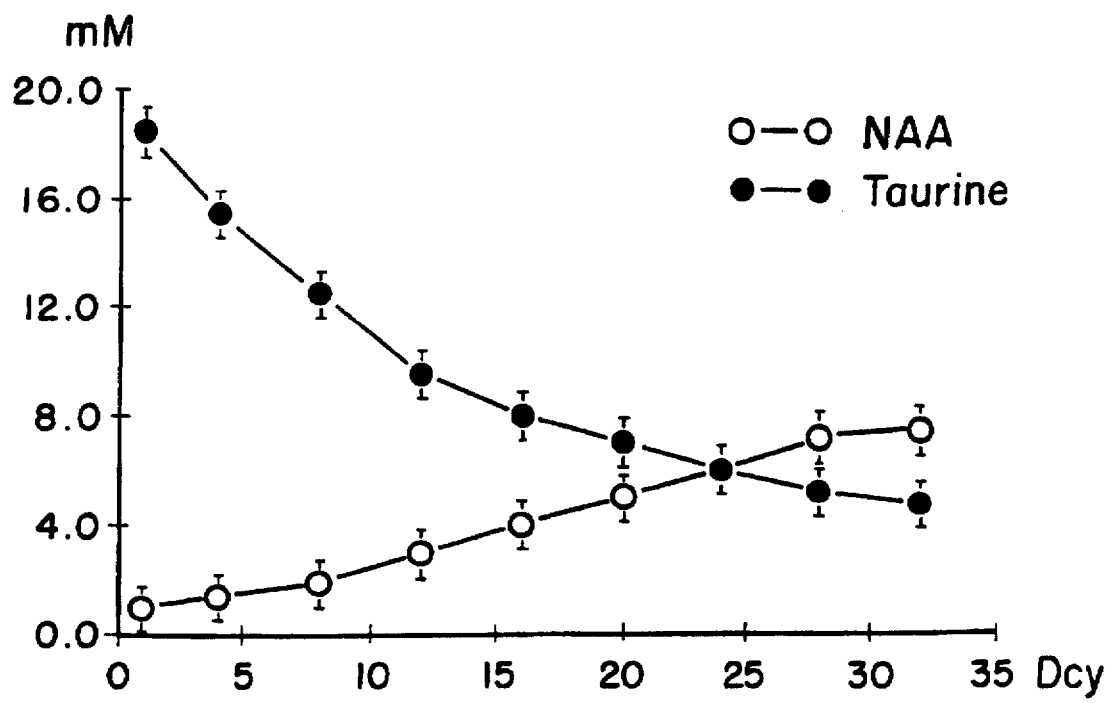
FIG. 7 shows the developmental changes in taurine and n-acetylaspartic acid levels in newborn and adult (32 day old) mice.

FIG. 6 is a representative high resolution proton spectrum of pup brain PCA extract showing the presence of creatine, inositol, taurine, choline and NAA, wherein the concentration of NAA is much lower than that of taurine in 10 day old pups. FIG. 7 is a summary of the developmental changes in brain taurine and NAA levels which show an inverse replacement correlation. As seen from FIG. 7, immediately after birth the level of taurine is around 18 mM while the level of NAA is only around 1 mM. At day 10, the level of taurine is already substantially decreased to levels around 11 mM, while the level of NAA is only about 2.5 mM, but increases steadily on daily basis. On day 26, both levels of taurine and NAA reach the same level of around 6 mM. The level of taurine then declines to around 4 mM at day 32, at which day the level of NAA reaches approximately 8 mM.

Figure 8:
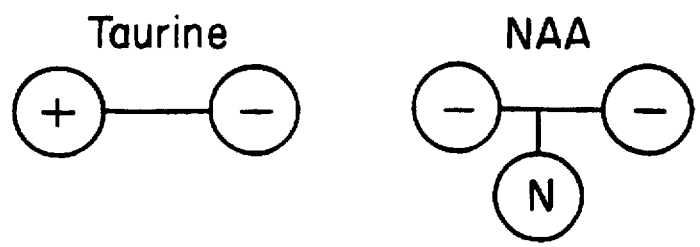
FIG. 8 illustrates a change in diffusion environment due to replacement of taurine with n-acetylaspartatic acid.

Replacement of taurine by NAA can thus far be summarized to accomplish two main effects on the intracellular environment: (1) changes in cytosolic buffer system from fetal, taurine containing type to adult, NAA containing, type; and (2) maintaining ionic balance after depletion of fetal taurine. In addition, replacement of taurine by NAA appears to have one more effect on the cytosol environment, namely, a change in the diffusion environment. At physiological pH, the main form of taurine is $NH_3^+\text{—}R\text{—}SO_4^-$ while most of NAA is in the form of —OOC—R—coo— as seen in FIG. 8.

Individual taurine molecules tend to attract, while NAA molecules tend to repel each other. It is conceivable, therefore, that passive diffusion of a negatively charged substrate such as ATP in cytosol may be faster in an NAA solution than in a taurine solution. ATP is a molecule which requires delivery from its production site (mitochondria) to the main consumption site (plasma membrane) by passive diffusion in the cytosol. Oxidative phosphorylation in mitochondria is much more active in adult brain than in fetal brain. ATP consumption at the Na-K pumps is also much more active in adult brain than in fetal brain. Therefore, faster ATP diffusion within the cytosol is desirable in mature brain. NAA replacement of taurine may indeed positively affect ATP diffusion in cytosol, however it definitely affects negatively the buffering capability.

Said phenomenon, i.e., the existence of taurine in newborn rats and its subsequent substitution with N-acetylaspartic acid indicates that the cerebral cells of newborn rats just after birth are provided with an additional buffering function to prevent the increase of the hydrogen ion concentration therein. However, such buffering function is rapidly lost with time. Its presence explains why newborn mammals show significant resistance to oxygen deficiency in comparison with adult animals or humans.

While the rapid control of acidosis is readily available to the normal and healthy adult mammal, including human being, and to a certain degree, even to a newborn baby, the fetus in utero cannot take advantage of this rapid adjustment system since the fetal $pCO_2$ is heavily dependent on factors, such as placental blood flow and maternal $pCO_2$, uncontrollable by the fetus itself. Therefore, it seems likely that the fetus has an alternative means of maintaining acid-base homeostasis.

Since taurine has been shown to be present in extremely high amounts in the brains of fetus and newborn mammals, the function of taurine as a buffering compound has been examined and the taurine-like buffering systems are described in this invention. These systems are use used to counter the acidotic changes in adults which, for any reason have their normal buffering system is damaged, inefficient or which cannot sufficiently counter severe acid-base disbalance.

Taurine is ubiquitous in mammalian organs. Taurine levels are especially high in the brain of the fetus reaching 18 mmol/1 in rat and rapidly declining after birth to adult levels of 4 mmol/1 in adult rat. Although the nutritional aspects of taurine are often emphasized, the majority of taurine in the brain exists as the free amino acid in the cytosol and is thought to be metabolically inert. At physiological pH, virtually all taurine is in the form of $R\text{—}SO_3^-$ and can be considered to be a weak acid such as $R\text{—}NH_3$, with a pKa value of 8.74, as shown below.

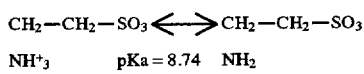

$NH^+_3 \qquad pKa = 8.74 \quad NH_2$

Based on the high levels of taurine in the fetus and in early life, on its presence in the cytosol, and on its buffering capability shown above, the current discovery proposes that the fetal taurine is a part of the cytosolic buffer and in the fetal brain it optimizes cytosolic buffering capacity at physiological pH and that in this way it would be also useful in compromised adults in the same way as in fetus or infants, if delivered in an appropriate form.

Although the compound taurine has a pKa=8.74, it alone has doubtful physiological function. However, if combined with carbonate (pKa=6.12) it would conceivably provide a useful buffering system. In the process of this invention, taurine analogues and taurine-like compounds have therefore been used to prepare taurine/carbonate or taurine-like/carbonate buffers and such buffers were investigated for their possible role as the acid-base control. Using the standard pH of interest, two buffer solutions with different pKa values, i.e., taurine/carbonate and taurine-like/carbonate buffers were prepared, wherein compounds in the appropriate molar ratio were mixed.

Brain carbonate levels at physiological conditions are estimated to be 23 mmol/l in rats, while taurine levels in rat fetal brain were shown to be 18 mmol/l. Theoretically thus, a mixture of physiological carbonate buffer having pKa 6.12 and the physiological taurine buffer having pKa=8.74, in a molar ratio of 23 to 18, provides a buffer solution with a newly optimal pKa value of 7.27. Therefore, it appears that cytosol of fetal brain indeed has a buffering capacity optimal at physiological brain pH.

In the same manner, other taurine analogs, such as guanidinoethane sulfate (GES), guanidinoethanesulfonic acid or taurine-like compounds having similar properties, are useful as active compounds of this invention. Metabolic acidosis is combatted not only by buffering compounds of this invention, but also by alkaline shifter agents of this invention such as GES and its derivatives and/or analogs.

GES is a taurine analogue which effectively competes with and inhibits taurine transport into the brain. Surprisingly, GES has been now demonstrated to be also an effective alkali shift agent of intracellular brain pH. GES crosses the blood brain barrier in the uncharged form and diffuses in the cytosol where it establishes the ratio between uncharged and charged forms according to equilibrium of cytosolic pH and pKa value of GES. Because the guanidino moiety has the high (12.48) pKa value, virtually all GES in brain cytosol is in charged form. The charged GES replaces intracellular taurine resulting in a shift of brain pH toward a higher, more alkaline pH value. GES possesses the unique property as alkali shift agent.

Similarly to GES, other compounds which have high pKa values, cross blood brain barrier in the uncharged form and are able to displace or replace taurine are effective alkali shift agents. These compounds are for example aminomonosaccharides, such as 2-amino-deoxyglucose and 3-amino-deoxyglucose; sulfonic acid derivatives of naturally occurring amino acids, such as asparagine and tryptophan; piperidino compounds, such as piperidine, pipecholic acid, and pyrrolidine; morpholino compounds such as 3-(n-morpholino) propanesulfonic acid; piperazino compounds such as N-2-hydroxyethylpiperazine-N'-ethanesulfonic acid and N-2-hydroxyethylpiperazine-N'-propanesulfonic acid, amantadine, isoniazid, aminosalicylic acid, chlordiazepoxide, cimetidine, carbamazepine bromocryptine, and di-β[morpholinoethyl]selenide.

Figure 4:
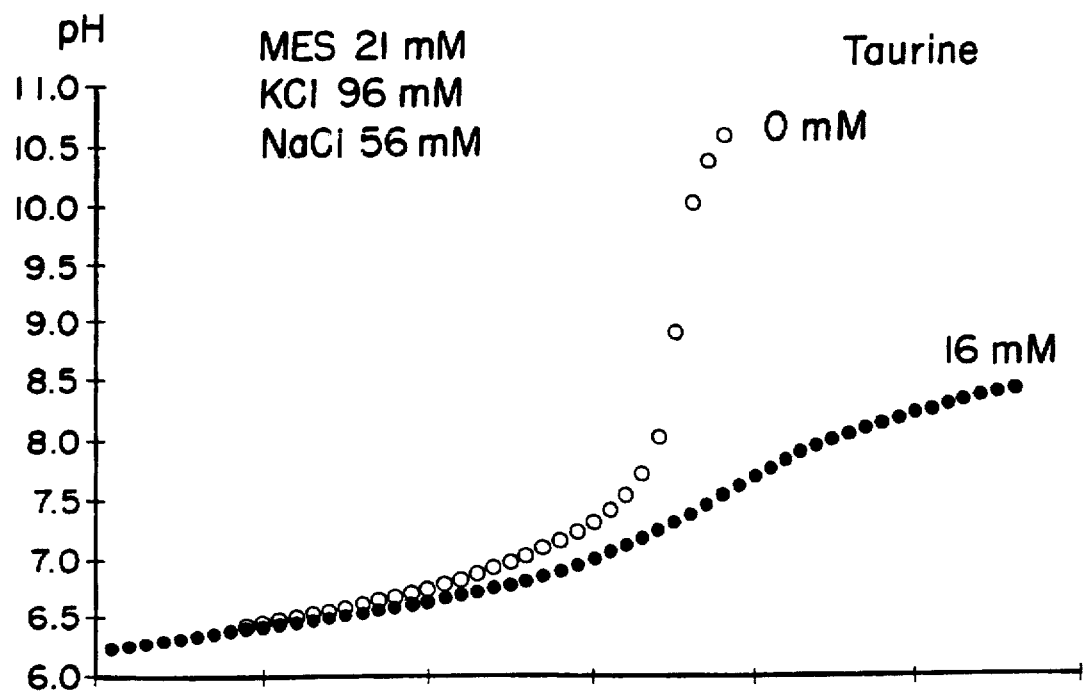
FIG. 4 illustrates the optimization of the 2-(N-morpholino) ethanesulfonic acid buffer system containing taurine.
Figure 5:
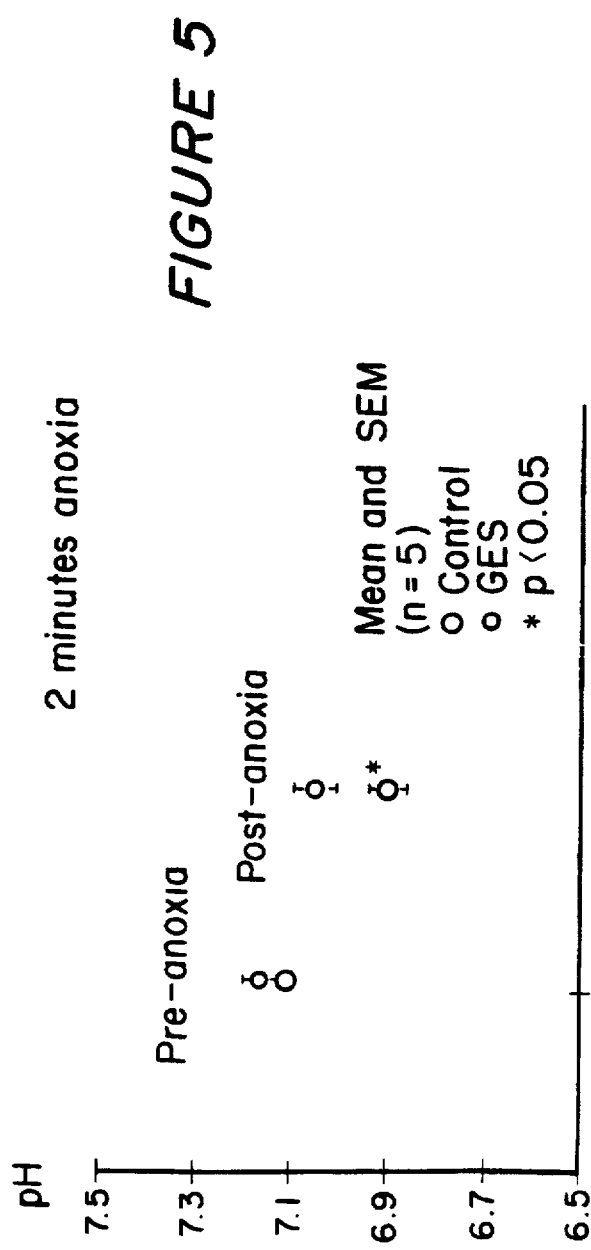
FIG. 5 illustrates the pH changes following the 2 minutes anoxia in the brain of control and GES pretreated adult mice.

Also as illustrated in FIG. 4, taurine can also optimize the buffer effect when added to 2-(N-morpholino) ethane sulfonic acid (MES) buffer (pka 6.1) in the same physiological concentration as that of brain carbonate, to result in taurine/ MES buffer of around pH 7.2. The MES buffer is used as the carbonate buffer equivalent for in vitro titration studies because it does not involve gaseous $CO_2$.

The pKa values of inorganic phosphate (Pi), adenosine diphosphate (ADP) and adenosine triphosphate (ATP) relevant to the maintenance of the physiological pH are 6.80, 6.88 and 6.95, respectively. The estimated normal levels of these components in the rat brain are 0.4 mmol/l for ADP and 3 mmol/l for ATP. Under normal conditions, the estimated potential contribution of Pi to the cytosol buffer is 0.6 mmol/l. If the contribution of ATP/ADP/Pi is taken into account, the cytosol buffer solution is optimal at pH 7.23, a very close pH to taurine/carbonate buffer of pH 7.27.

The substance useful as the active component of the buffering system in the method of this invention is non-toxic, is able to cross the blood-brain barrier and/or is cell membrane permeable, and possess a buffering action for the hydrogen ion concentration. For alkaline shifting systems in the method of this invention, the active component is non-toxic, is able to cross the blood-brain barrier and/or is cell membrane permeable, has pKa higher than 6.8, preferably not above 11, and is able to shift intracellular pH to a more desirable alkaline level to combat metabolic acidosis.

Based on the above-stated criteria, the requirement for the compound useful in practice of this invention is as follows.

The alkali shifting or buffering compounds that are useful as an active component of the buffering system of the method of this invention are non-toxic, either endogenously present in the cells or synthetic, contain nitrogen and are permeable through the cell membrane in tissue cells, such as brain cells, and/or are able to pass the blood-brain barrier. The compounds are able to exert a buffering action on the hydrogen ion concentration in those cells suffering from lactic acidosis under the condition of oxygen deficiency. The active compound has preferably a pKa of not less than 6.8.

In general, nitrogen-containing compounds behave as a weak basic substances, and their ionic type molecules and non-ionic type molecules coexist in physiological solutions. The ionic type molecules have difficulty to permeate through cell membranes (except when actively transported through the membrane in kidneys cells, for example), while the non-ionic type molecules are cell membrane permeable due to a diffusion mechanism restricted by a lipid barrier.

When the non-ionic type molecules which permeate through a cell membrane reach a concentration equilibrium on both sides of the cell membrane, the ratio of the concentration of a nitrogen-containing compound inside to outside of the cell membrane can be expressed by the following equation:

$$\frac{C_{in}}{C_{out}} = \frac{1 + 10^{pKa-pH\,(in)}}{1 + 10^{pKa-pH\,(out)}}$$

wherein $C_{in}$ and $C_{out}$ are, respectively, the concentrations of the nitrogen-containing compound at the inside and outside of the cell membrane. pKa is the pKa value of the nitrogen-containing compound, and pH(in) and pH(out) are respectively the pH value at the inside and outside of the cell membrane.

As understood from this equation, the concentration of the nitrogen-containing compound in cells is increased when its pKa value is higher than the pH value inside the cell. Thus, the use of a nitrogen-containing compound having a pKa value higher than that of blood plasma (i.e., 7.4) is desirable in order to favor entry of the compounds into cells to increase the concentration of said compounds available for buffering excess hydrogen ions.

The active substance of the buffering system behaves generally as a hydrogen ion acceptor and is expected to exert a buffering action against the increase of the hydrogen ion concentration. The active substance may be chosen from heterocyclic compounds, either monocyclic or polycyclic where the hetero atom is nitrogen containing compounds having at least one of the following and where a functional group: $-NH_2$, $=NH$, $\equiv N$, $C=N-$, is attached to the heterocyclic compound directly or through an alkyl group.

The exemplary buffering compound of this invention is the taurine-like compound, and all taurine endogenous and synthetic analogs, such as guanidinoethane sulfate. Other compounds having the same or similar properties as taurine and possessing the required buffering capability which may be either inhibitors and/or competitors of taurine are equally contemplated to be within the scope of this invention.

Three categories of mechanisms may be involved in reduction of the severity of the consequences of lactic acidosis, namely, raising intracellular acid buffering capacity (category I compounds), shifting the intracellular pH to a more alkaline range (category II compounds), and decreasing generation of lactic acid. Among these three mechanisms, the former two are feasible for development into pharmacologic agents. Taurine is a representative compound in category I, i.e., adding intracellular acid buffering capacity. Guanidinoethane sulfonic acid (GES) is a representative compound in category II, i.e., shifting intracellular to a more alkaline range (alkaline shifter).

As indicated above, two distinct mechanisms for neuroprotection from irreversible injury due to lactic acidosis from anoxia/ischemia have been identified. Accordingly, the specified chemical compounds acting as agents which protect cells from irreversible injury due to lactic acidosis from anoxia/ischemia can be categorized into two groups of acids buffering compounds and alkaline shifters.

Acid Buffering Compounds

Compounds in this category have as their neuroprotective mechanism against anoxia/ischemia the ability to confer to endogenous intracellular cytoplasmic buffer an additional buffering capacity towards the hydrogen protons of lactic acid generated by anaerobic glycolysis. Efficacy in vivo is predicated on compounds having a pKa of no less than 6.8 and no greater than 8.4. Additionally, for neuronal protection, compounds must be able to enter brain cells and therefore must be able to cross blood-brain barrier.

Alkaline Shifters

Compounds in the second category have as their neuroprotective mechanism against the deleterious effects of anoxia/ischemia the ability to shift intracellular pH to a more alkalinic range (alkaline shifter), thereby decreasing the acidifying effect of the protons of intracellular lactic acid generated by anaerobic glycolysis. Compounds in these categories must have a pKa value of no less than 8.4 and higher than 11.0. To confer neuronal protection, compounds must be able to penetrate brain cells and therefore must be able to cross blood-brain barrier.

Compounds used in the protection of neuronal cells against intracellular lactic acidosis generated by anaerobic glycolysis during anoxia/ischemia, as described above, include amino-monosaccharides, such as 2-amino-deoxyglucose and 3-amino-deoxyglucose; sulfonic acid derivatives of naturally occurring amino acids, such as asparagine and tryptophan; piperidino compounds, such as piperidine, pipecholic acid, and pyrrolidine; morpholino compounds such as 3-(n-morpholino)propanesulfonic acid; piperazino compounds such as N-2-hydroxyethylpiperazine-N'ethanesulfonic acid and N-2-hydroxyethylpiperazine-N'propanesulfonic acid.

Additionally, specific compounds which do not fall into any of the above categories but which are currently available for human use can also potentially be used as neuroprotective agents in anoxia/ischemia. They were selected based on their chemical structure and the fact that they are known cross blood-brain-barrier and to enter brain cells. These compounds are amantadine, used in the treatment of Parkinson's disease and prevention for influenza, isoniazid, an antituberculous agent also used to treat and reduce chorea, a central nervous system disease, aminosalicylic acid, an antituberculous agent, and other compounds such as chlordiazepoxide, cimetidine, carbamazepine bromocriptine, di-β[morpholinoethyl]selenide (PIPSE), di-β[morpholinoethyl]selenide (MOSE), (N,N, N-trimethyl-N'-[2-hydroxymethyl-5-iodo-benzyl]propyl-diamine (HIPDM), and para-iodoisopropylamphetamine.

Other suitable compounds of this invention include other derivatives of morpholino compounds as 2-(N-morpholino) ethane sulfonic acid wherein the functional group of morpholino compound bound to the hetero nitrogen atom or alkyl group is $NH_2$; $=NH$; $\equiv N$; or $=C=N-$.

To test the taurine buffering capability during anoxia, the taurine/carbonate buffer was tested in neonatal brains and the acid-base balance of neonatal brains in response to anoxia was evaluated by new approach using in vivo NMR spectroscopy. Research on brain acid-base equilibrium has been previously hampered by technical limitations. The development of nuclear magnetic resonance (NMR) in vivo spectroscopy has provided unprecedented opportunities in the research of acid-base balance of the brain. Now, intracellular pH and lactate measurements can be readily performed in live animals under various conditions using proton ($^1H$) and phosphorous ($^{31}P$) NMR spectroscopy.

A Nicolet NMR System NT-200 (4.7T) was used for NMR experiments. Mice, rats or pups (Sprague-Dawley) were lightly anesthetized with ketamine hydrochloride, 50 mg/kg I.P., and placed in the NMR probe which contained an oval surface coil (one turn, 8×12 mm diameter) tunable to the resonance frequency of the proton and $^{31}P$. To eliminate signal contamination, scalp and temporal muscle were retracted. Field homogeneity was maximized by skimming on water proton signals. To produce anoxia, 100% nitrogen gas was rapidly infused (14 l/min) into the probe chamber. Anoxia could be reversed by infusion of air. Calibration studies using an oxygen meter (OM-1 Biological oxygen Meter, Micro-electrodes, Inc.) confirmed that this technique produced complete $O_2$ depletion in the chamber or its reversal within 1 minute. $^1H$ spectra were obtained at 199.97 MHz=z using a 1331-τ-2662 spin echo sequence with a τ delay of 68 ms (spectral width: 2 KHz, memory block: 4K, recycle time 2.7 seconds). The interpulse delay of the Hore sequence was adjusted so that the lactate resonance experienced least attenuation. $^{31}P$ spectra were obtained at 80.99 MHz using a one pulse sequence (spectral width: 6 KHz, memory block: 4K, recycle time 2.7 seconds). The free induction decay (FID) like signals from remaining water proton signals were eliminated by applying sine function anodization. The broad resonance with short $T_2$ on $^{31}P$ NMR spectra was removed using the convolution difference technique. Line broadening of 5 Hz and 30 Hz were applied as noise filter for proton and $^{31}P$ spectra, respectively. Intracellular pH was calculated using the equation: $pH=6.77 \log (\delta-3.29)/(5.68-\delta)$, where $\delta$ is the chemical shift of inorganic phosphate (Pi), referred to that of phosphocreatine (PCr) as obtained by this technique.

Figure 2:
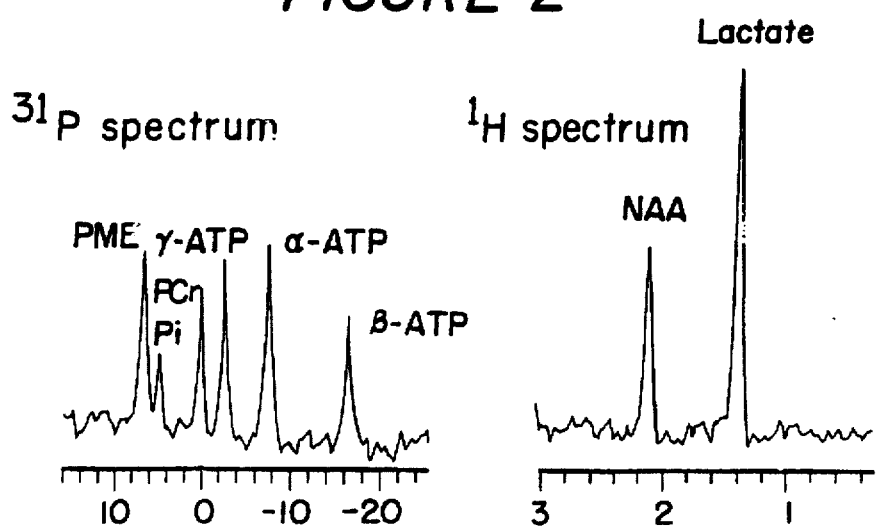
FIG. 2 represents $^{31}$p spectrum of the brain of 10 day old rat pups following 7.5 minutes of anoxia.
Figure 3:
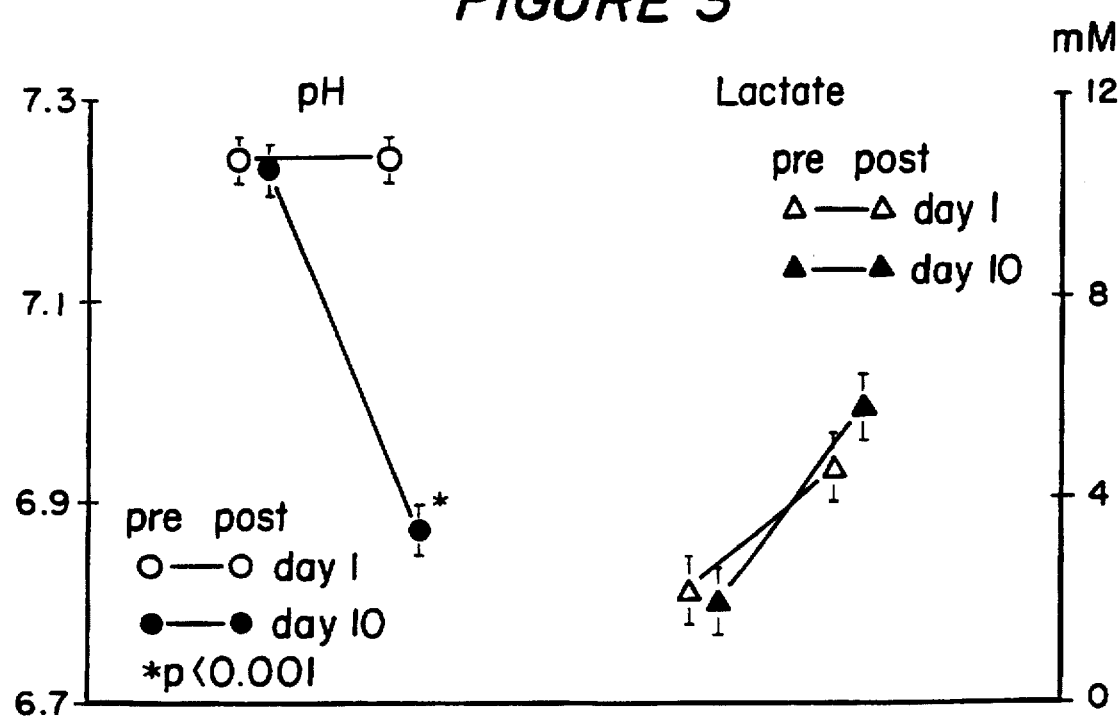
FIG. 3 shows changes in intracellular pH and lactate levels of 1 day and 10 day old pups following 7.5 minutes anoxia.

FIG. 2 shows representative proton and $^{31}P$ spectra of 10 day old pups following 7.5 minutes of anoxia. FIG. 3 summarizes the results obtained by measurement of intracellular pH and lactate levels in 1 day (n=10) and 10 day old pups (n=10) following 7.5 minutes of total anoxia. Brain taurine levels were 18 mmol/l and 11 mmol/l for day 1 and day 10 pups, respectively. The remarkable ability of 1 day old pup brain to preserve normal pH in spite of significant accumulation of lactate was observed.

When the comparison was made between the control group of newborn rats and the experimental group injected with taurine in the amount of 16 mmol/kg/day of taurine for 2–10 days and both groups were subjected to anoxia, according to Example 1, the pH in the brains of newborn rat pups pretreated with taurine was only slightly decreased following the anoxia to pH 7.0 from 7.3 before anoxia, while the brain of the control group dropped to pH 6.85, which pH would sooner or later lead to brain cells injury and death.

At the same time, the amount of lactic acid in both the experimental and control groups increased substantially from preanoxia level of 0.7, expressed by the lactic acid/N-acetyl aspartate, to 2.4 post anoxia. There was no difference observed between the experimental and control groups.

The above results indicate that anaerobic glycolysis due to anoxia proceeds in both the experimental group and in the control group and leads to accumulation of lactic acid to the same extent in both groups. To the contrary, the pH depression is considerably prevented in the experimental group by the buffering action of taurine administered as a pretreatment to the experimental group, while the pH drops to a dangerous limit in the control group which was not pretreated with taurine.

Similar results were observed and are illustrated in FIG. 3. One day and ten days old pups were submitted to 7.5 minutes of anoxia and their pH values and lactate levels before and after the exposure were determined. As seen in FIG. 3, pH level in one day old pups did not change even after 7.5 minutes anoxia, while the pH in ten day old pups dropped to dangerous levels of 6.85. The lactate level was similar in both groups.

The depression of the intracellular pH caused by lactic acidosis in anoxia can thus be prevented by the buffering activity of an active compound, such as taurine, or other taurine-like compound which has a buffering activity at or below physiological pH. In other words, the resistance to anoxia is expected to increase when the active compound having the same behavior and properties as taurine is administered before the induction of anoxia.

Compounds of this invention that are effective in combatting metabolic acidosis, also function by shifting the intracellular pH to a more suitable alkaline level. One of the taurine-like compounds useful in the practice of the current invention is guanidoethanesulfonic acid or guanidinoethane sulfate. Guanidinoethanesulfonic acid is known to have ability to cross the blood-brain barrier (*J. Pharmacol. Exp. Ther.*, 211:465–471 (1980)). The pKa value of its amidine residue is 12.48. Guanidonoethane sulfate (GES), an analog of taurine has shown similar protective properties to taurine, when administered to adult mice prior to exposure to anoxia. Under the experimental conditions described in Example 3, after 2.5 minutes of anoxia exposure, adult mice pretreated with GES had a zero mortality rate. Both control groups of adult mice pretreated with either taurine, which does not cross the blood-brain barrier in adult mice, or with physiological saline, and exposed to 2.5 minutes of anoxia experienced 40% mortality. When the anoxia period was extended to 2.75 minutes, the GES treated mice had 2 mortality rate of 20%, while the control groups' mortality rate, whether taurine or saline pretreated, reached 100%. Additional data regarding the neuroprotective property of GES demonstrate that GES protects neurons in the CA1 region of the hippocampus, a structure extremely sensitive to anoxia/ischemia from delayed cell death as result of ischemia.

FIG. 1 illustrates the results showing the protective function of GES against fatal injury to the cells caused by drop in the pH. When compared to taurine and saline pretreated groups, as seen in columns 1–4, the pretreated group with GES provided 100% protection against 2.5 minutes long anoxia (column 1), while taurine, which does not cross the blood-brain barrier in adult (column 3), was only providing protection in 40%. 60% of the animals died in taurine and saline groups. Thus, there was no difference between taurine pretreated animals (column B) and saline pretreated animal (columns 2 and 4). Seemingly, the saline control group (column 4) did better than taurine group (column 3).

The results were even more pronounced when the anoxia exposure is extended to 2.75 minutes. While the mortality in GES pretreated group (column 5) was 20%, mortality in all other three groups, i.e., taurine and saline pretreated groups, 6–8 was 100% and there were no survivors.

These findings clearly show that the cell permeable, blood-brain barrier crossing compounds, which are taurine analogs, are able to provide excellent protection against the detrimental effects of oxygen deficiency and in this way protect the animal against irreparable injury due to the increase in hydrogen ion concentration which would otherwise lead to cell death.

These results also show that for the short time anoxia exposure, the pretreatment of adult animals with GES is more effective than pretreatment with taurine or saline and can completely protect the animal from any detrimental effect caused by oxygen deficiency and prevent the injury of the cells due to lactic acidosis.

When the time of anoxia is extended to longer time, GES protects the adult animals to the extent that only 20% of all animals die while all taurine or saline treated animals die.

In the similar experiment, adult mice were used for determination of pH changes depending on pretreatment with GES prior to anoxia induced with nitrogen. The pH of the animals' brain in vivo was measured using NMR, before and after the nitrogen exposure. The average pH values in the brain before the anoxia were 7.16 for GES treated animals and 7.11 for saline treated animals. Thus, before anoxia, the difference was not significant. Following the exposure to pure nitrogen atmosphere, i.e., after anoxia period, the pH values in the GES treated animals were pH 7.05, while the pH value in the control, saline treated animals, was dangerously low at pH 6.90. Thus, the administration of GES significantly ($p<0.05$) prevented the decrease in the cellular pH in the animals' brains and prevented the brain injury in adult animals which normally do not possess the mechanism which would prevent such a pH drop.

When the newborn 1 day old rat pups were tested against 10 day old pups and their levels of lactic acid and pH in the brain were determined in vivo using NMR spectroscopy, the one day old pups had an extraordinary ability to preserve normal pH even after 7.5 minutes anoxic exposure. As seen in FIG. 3, in 1 day old pups (0—0) the pH prior and post anoxia was absolutely unchanged. To the contrary, for the 10 day old pups, (0—0) the post anoxia pH dropped sharply to levels under pH 6.9, which would cause irreparable injury to central nervous tissue.

In the same group, the level of taurine in the one day old pups was around 18 mmol/l while the level of taurine in 10 day old was around 11 mol/l.

When the levels of lactic acid were measured in the same two groups of 1 and 10 days old pups, as seen in FIG. 3, both groups experienced a similar increase in levels of lactate from around 2 mM to 5–6 mM. Thus the intracellular metabolism in both groups was very similar, but in 1 day old pups, the high level of taurine was able to preserve the normal physiological pH, while the 10 day old pups were subjected to a dangerous drop in pH due to tissue acidosis and to insufficient buffering capacity of available buffering systems.

This experiment clearly illustrates advantages of the current invention by providing an additional buffering system able to compensate for metabolic acidosis caused by insufficient supply of oxygen and metabolic over production of lactic acid and hydrogen ions.

Recent studies indicated that GES in brain cytosol may function as additional alkali which in turn protects brain pH against intracellular lactic acidosis. GES has been shown to enhance the survival rate of mice exposed to anoxia. The protective effects of GES on delayed CA1 neuronal death using a gerbil model of forebrain ischemia was investigated. Pretreatment with GES (675 mg/kg/day IP for 2 weeks) showed significant nueroprotection on CA1 neurons studied 7 days after 5 minutes bilateral carotid occlusion. The result indicates that intracellular acidosis likely plays a role in mediating the harmful effects of ischemia, perhaps in the early steps of a deleterious cascade leading to excitatory amino-acid excess. Results are described in Example 6 and in FIGS. 9 and 10.

As demonstrated in FIG. 9, there is a detectable shift in intracellular pH, to a more alkaline level, for mice treated with GES, when compared with mice treated with either taurine or saline. That shift is evident both before and after anoxia was induced. While in adult animals taurine per se was not effective, because it does not cross the blood brain barrier, the protection by taurine pretreatment was seen in newborn or very young animals.

Figure 10A:
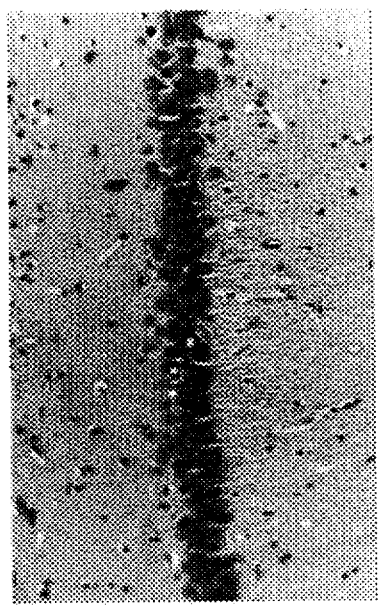
FIG. 10A, 10B, and 10C represent photomicrographs depicting neuronal density for control, saline ischemia and GES ischemia in gerbils.
Figure 10B:
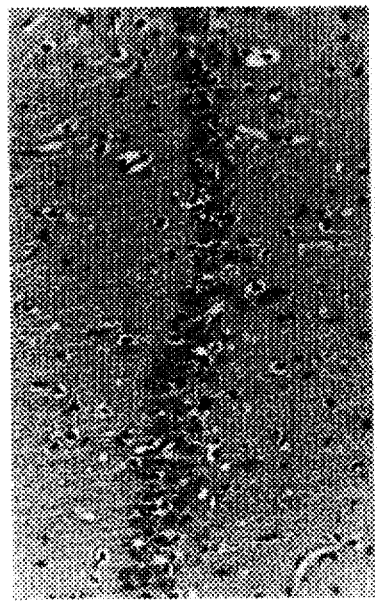
Figure 10C:
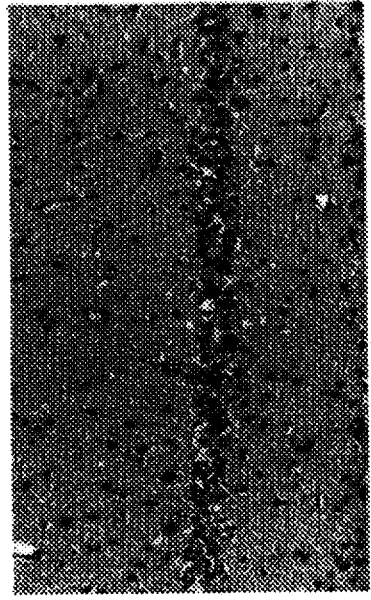
Figure 11:
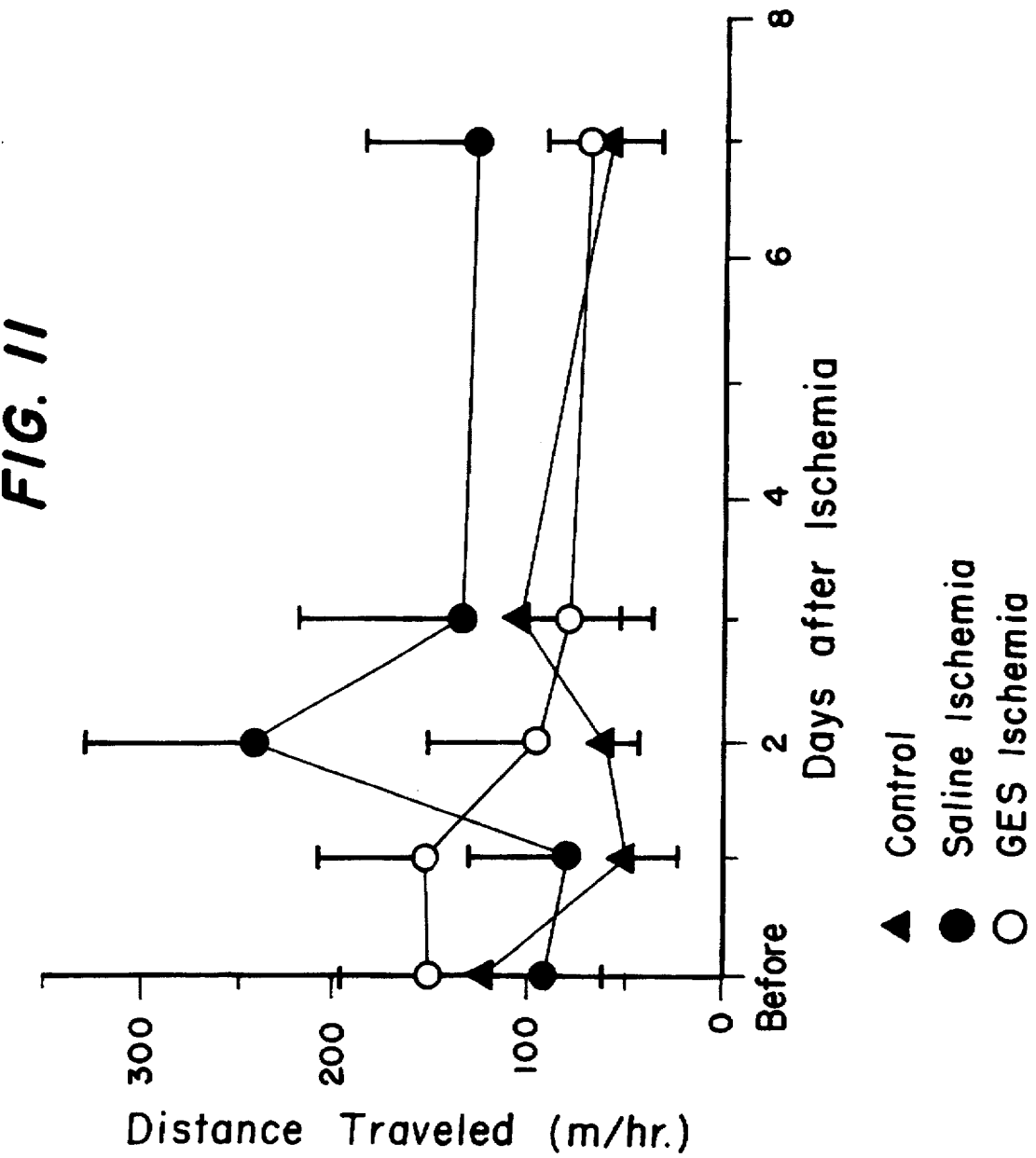
FIG. 11 illustrates the effect of GES in post-ischemia hyperactivity.

Alkaline shifting property of GES is illustrated in FIGS. 9–13 and in Examples 6 and 7. FIG. 9 shows representative $^{31}P$ spectra of gerbil brain utilized for intracellular pH determination. PME means phosphomonester, Pi means the representative amount of inorganic phosphate, PDE represents phosphodiester, PCr is phosphocreatine and ATP means adenosine triphosphate. Administration of GES has been shown to shift the pH from 7.17 to 7.26 which is about a normal physiological level (Table 2). FIG. 10 are representative photomicrographs of the CA1 neurons region of the gerbil brain. Panel A depicts a photomicrograph taken of the control group; Panel B depicts a photomicrograph taken of the animal of group treated with saline submitted to ischemia. Panel C depicts a photomicrograph of the animal brain of the animal treated with GES and submitted to ischemia. As clearly seen from the comparison of Panels B and C, there is much higher neuronal density of viable neurons present in the animals treated with alkaline shifter GES. Results are summarized in Table 3. Significantly higher neuronal density was observed in the GES ischemia than saline ischemia group. Similarly, GES was shown to normalize and counter the hyperactivity observed in animals with induced ischemia, as seen in FIG. 11 where the saline control following the induced ischemia experienced extended hyperactivity as measured by travelling distances. GES pretreated animals did not experienced such hyperactivity periods and their behavioral response to ischemia was corresponding to that of control non-ischemic animals. Biochemically, these GES treated animals had alkaline shift toward higher (7.26) pH compared to the saline controls which had lower pH~7.17. Such shift in pH was clearly responsible for near to normal response to ischemia and lack of ischemic damage due to lactic acidosis and anoxia.

This experiment clearly confirms that alkaline shifter compounds are able to counter deleterious effect of lactic acidosis in brain cells and are effective in preventing and treating unnatural biochemical, biophysical or metabolic changes in the brain cells.

In example 7, a new category of agents, brain pH alkaline shifters, is described. Using a prototype agent, guanidoethane sulfate (GES), the actual alkali shift in pH in adult mice brain was demonstrated by 31-phosphorous ($^{31}P$) nuclear magnetic resonance (NMR) in vivo spectroscopy. Such an alkaline shift effectively reduced brain intracellular lactic acidosis brought about by anoxic insult supporting the notion that a pH alkaline shift may protect brain against the deleterious effects of anoxia/ischemia. Since higher pH has been shown to significantly reduce beta-amyloid deposition, alkaline shifters may also be utilized as a treatment agent for Alzheimer's disease.

Guanidoethane sulfate (GES) is a taurine analogue originally introduced as a competitive inhibitor of taurine transport into the brain. The chronic administration of GES in mice has been shown to result in gradual replacement of brain taurine by GES. The majority of taurine and GES in mice brain are believed to be metabolically inert and exist in the brain cells as free cytosolic molecules. Entry of taurine or GES across the blood-brain-barrier is likely to be in the uncharged form, $R-NH_2$. Following free diffusion into cytosol, the ratio between charged ($RH_3^+$) and uncharged forms will equilibrate according to cytosolic pH and their respective pKa values. The pKa value of the amino moiety of taurine is 8.74, whereas the pKa value of the guadino moiety of GES is 12.48. Accordingly, virtually all GES is in the charged form after entering brain cells, while 1/38 of taurine remains uncharged. Therefore, during the process of equilibration, the equivalent number of GES molecules intracellularly extract more protons (stronger alkali) out of the cytosol than the equivalent number of taurine molecules. Theoretically, the accumulation of GES in brain (either by equivalent replacement of taurine or in addition to taurine) result in a shift of brain pH towards a more alkaline value. GES therefore, can be utilized as alkaline shift agent.

Accordingly, the following hypotheses were examined in adult mice. (1) Is GES administration sufficient to produce significant accumulation of GES in brain results in alkaline shift of brain pH? and (2) Does this alkaline shift effectively reduce the level of brain lactic acidosis brought about by anaerobic glycolysis associated with anoxic/ischemic insult?

Figure 12:
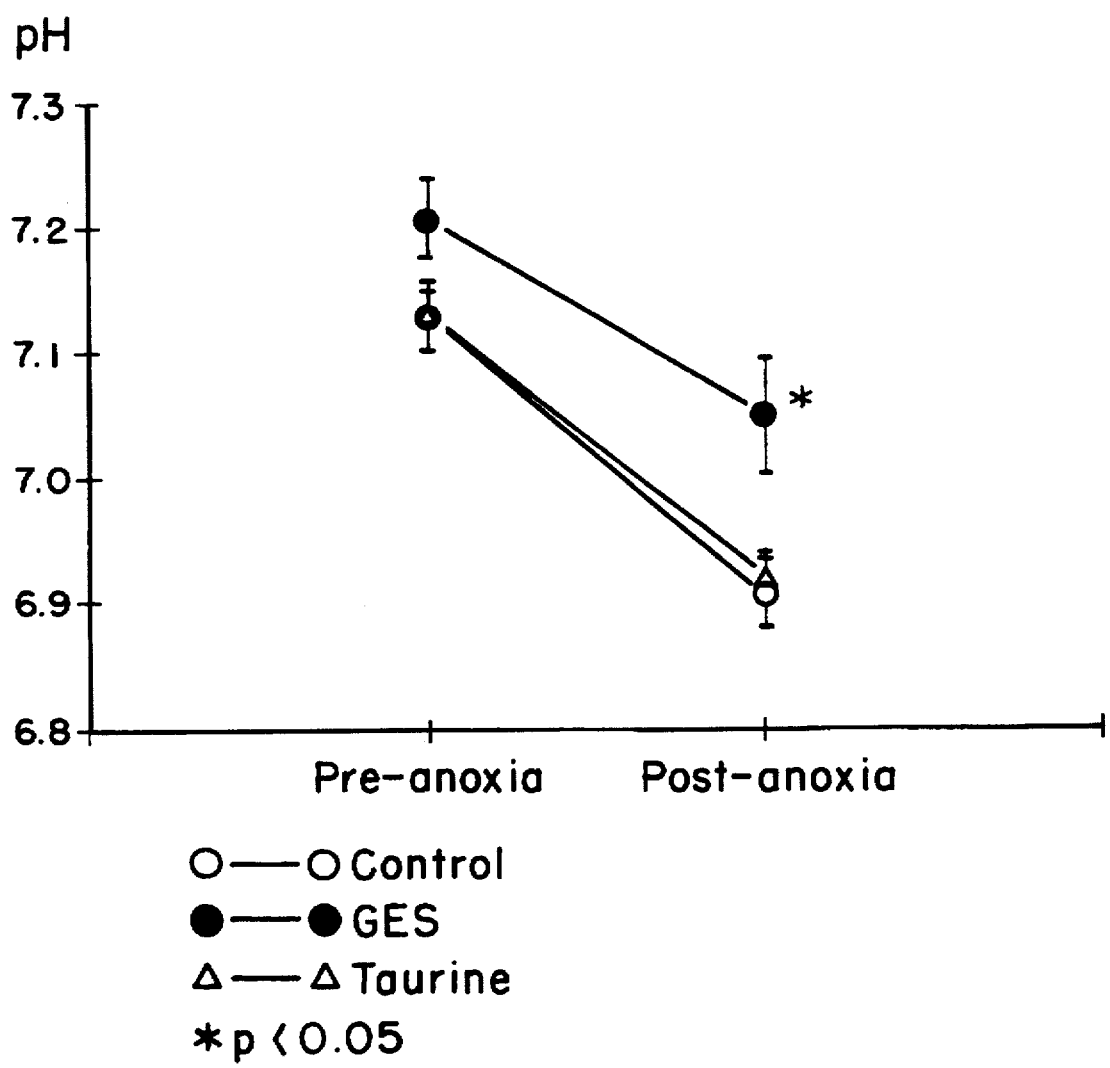
FIG. 12 illustrates the alkaline shift in brain intracellular pH in GES pretreated mice, in both pre-anoxia and post anoxia states.
Figure 13:
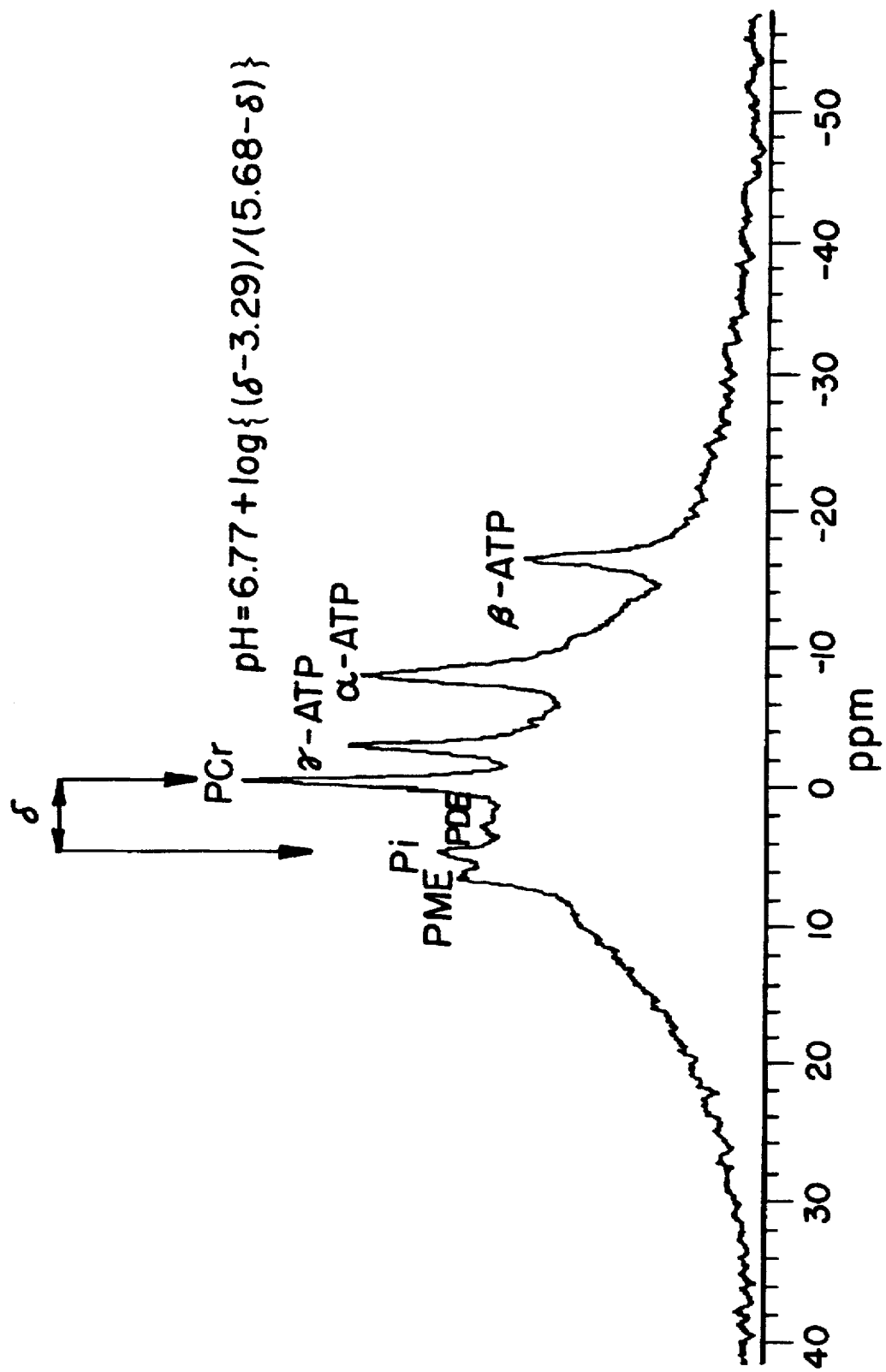
FIG. 13 illustrates representative $^{31}P$ spectra of mouse brain used for intracellular pH determination.

Results are described in Example 7, FIGS. 12 and 13 and in Table 4.

FIG. 12 illustrates brain intracellular pH for control, GES, and taurine groups. There is clear alkali shift of GES group in pre-anoxia compared to other two groups. Such alkali shift is maintained following 12 minutes of post anoxia. Plot is shown with mean and standard error of means.

Animals which received GES or taurine supplementation did not show any observable adverse effects in their behavior or respiratory pattern. FIG. 13 is a representative $^{31}P$ spectrum of mouse brain used for intracellular pH determination. Brain pH of pre- and after 2 minutes anoxia are shown in FIG. 12. High GES levels significantly increased brain intracellular pH (alkaline shift), while arterial blood gas parameters including pH remained essentially unchanged (Table 4). With anoxia, brain pH became more acidic in all three groups. However, brain pH of the GES group remained higher, retaining the degree of alkaline shift. Lactate levels post 2.5 min. anoxia were essentially identical among the three groups (Table 4) demonstrating that there was no significant difference in activities of anaerobic glycolysis among the three groups.

The present study supports both hypotheses proposed, i.e., (1) GES produces an "alkaline shift" in brain pH, and (2) the alkaline shift reduced brain acidosis under anoxic conditions. GES therefore, can be categorized as a prototype agent of an entirely novel category of alkaline shifters and compounds in this category can be utilized as brain protective agents against the deleterious effects of intracellular lactic acidosis. Indeed, recent studies have demonstrated that GES significantly enhances the survival rate of adult mice exposed to anoxia and that GES behaves as neuroprotective agent toward delayed hippocampal CA1 neuronal death in the gerbil model of forebrain ischemia.

Hypothermia represents a well-known neuroprotective condition and also produces an alkaline shift in brain pH. The underlying mechanism promoting either the alkaline shift or neuroprotection by hypothermia is unknown. Primary energy failure is considered to play only a minor role, if any, in cellular mortality associated with anoxia/ischemia and, therefore, the hypometabolic state per se brought about by hypothermia is unlikely to be the sole factor in determining the neuroprotective effects of hypothermia. On the other hand, a hypometabolic state results in a decline in the production of lactic acid under anaerobic conditions. In combination with an alkaline shift, such a decline in lactic production significantly reduces the level of acidosis during anoxia/ischemia. Therefore, similarly to the GES alkaline shift protective activity, protection against lactic acidosis is achieved by induction of an alkaline shift by other compounds possessing the same alkaline shifting properties in hypothermic brain protection against anoxia/ischemia.

Beta-amyloid constitutes a major component of the senile plaques seen in Alzheimer's disease and is suspected to be a causative factor of Alzheimer's disease. The deposition of beta-amyloid has been observed to be pH dependent, with higher pH (within physiologic range) decreasing the extent of aggregation. Theoretically, an agent capable of shifting intracellular pH of the brain to the alkaline side, such as GES can retard or even prevent the progression of Alzheimer's disease. There is potential for the use of GES in the treatment of Alzheimer's disease.

The study represents further supportive evidence for the working hypotheses: (1) intracellular acidosis likely plays a role in mediating the harmful effects of ischemia including delayed neuronal death in the CA1 region of the hippocampus, perhaps in the early steps of a deleterious biochemical/biophysical cascade; (2) alkali shift represents another neuroprotective mechanism against the harmful effects of intracellular acidosis.

Hypothermia, another neuroprotective condition in anoxia/ischemia, is known to produce a brain alkali shift. Since acute energy failure is believed to be only a minor factor, if any, producing delayed neuronal death, such an alkali shift may play a significant role in neuroprotecting of hypothermia. The current study indicates that pharmacological manipulation of intracellular pH and, hence, protection towards delayed neuronal death feasible may to protect the brain cells from the detrimental effect of ischemia and anoxia.

UTILITY

It is now apparent that reduction of intracellular acidosis due generation of lactic acidosis is an effective means of preventing cell damage due to anoxia/ischemia.

The concept that lactic acidosis plays a key role in determining the outcome of brain anoxia/ischemia is now well recognized. Since it appears that acidosis is more harmful to brain than the lactate molecular per se, any condition which lessens the extent of brain acidosis associated with anoxia/ischemia should confer cytoprotective effects on brain tissue against anoxic/ischemic insults. Theoretically, there are three categories of conditions capable of preventing severe brain acidosis, namely, the conditions which: (1) limit lactic acid production; (2) permit a higher buffering capacity against lactic acid; and (3) shift baseline brain pH towards a more alkaline value. Indeed, previous studies have demonstrated favorable effects of the first two categories on the outcome of brain anoxia/ischemia.

The method and compounds of this invention may be used for protection of any tissue or cells from the irreversible damage and injury due to lactic acidosis. Buffering compounds are particularly useful for treatment of acute cerebral ischemia, stroke, subarachnoid hemorrhage, vasospasm induced ischemia in tissue, brain trauma, spinal cord injury, chronic obstructive pulmonary disease, sudden infant death syndrome, drowning, accidental electrocution, CO and $CO_2$ poisoning during cardio-pulmonary resuscitation, in post operative brain, cardiac or vascular surgery as a component of cardioplegic solution for preservation of organs for transplantation, prevention of delayed neuronal death due to transient ischemia, in protection of fetus or prematurely born baby in management of risk group such as soldiers, miners or construction workers. Any disease or conditions which may result in ischemia or anoxic injury of the brain and other critical organs can be successfully prevented and/or treated with such agents. Moreover, compounds of this invention that are effective in shifting intracellular pH to a more alkaline level may be used to combat metabolic acidosis as well as other conditions where an intracellular alkaline shift is beneficial, including Alzheimer's disease where the undesired deposition of beta-amyloid fibers in brain cells may be inhibited by an alkaline shift in intracellular pH.

The alkaline shifting property of alkaline shifter compounds is useful for treatment of other conditions here an intracellular alkaline shift is beneficial. Foremost among these is Alzheimer's disease. The principal pathologic changes in Alzheimer's disease are senile plaques and neurofibrillary tangles. Beta-amyloid represents the major component of senile plaques and is though to be a causative factor of Alzheimer's disease. Deposition of this beta amyloid has been observed to be pH dependent. Higher pH values (still within physiologic range) decreases the extent of beta-amyloid aggregation. Therefore, the property alkaline shifter compounds to shift intracellular brain pH to a more alkaline level is useful to inhibit deposition of amyloid fibers in brain and retard the progression of Alzheimer's disease.

The substances to be used as the active components in the method of this invention are different from the conventional drugs known and used up-to-date. The substances of this invention suppress the increase of the hydrogen ion concentration in cerebral cells caused by lactic acidosis. They either utilize their buffering action to reduce the action of the hydrogen ion in cerebral cells or effect a shift in intracellular pH to a more alkaline value, to prevent cell damage injury or death. The method of this invention can be used as the first aid in case of vasoconstriction or diminished of blood supply after cerebral infarction, ischemia, subarachnoid hemorrhage, cerebrospinal trauma etc., in both adults and newborns. In adults, the active compound will cross blood brain barrier, i.e., taurine-like compound or taurine analog. In newborns and infants, taurine and/or taurine-like compounds will be useful.

To a patient in need of such treatment, the compounds may be administered intravenously, orally, parenterally, through intravenous drip, or by intrathecal injection. In instances of diseases or injuries requiring blood oxygen supply, the treatment may be combined with or initiated by, for example, administration of thrombus removal agent such as streptokinase or by endarterectomy or angioplasty. However, even if oxygen blood supply is restored early, brain cells cannot endure over five minutes under anoxia. Therefore, the administration of the protecting agent of this invention alone or in conjunction with other drugs can be a life saving measure and the compounds of this invention will be able to ensure prolongation of cellular survival time to 20 to 30 minutes which will be sufficient to obtain the appropriate treatment.

The treatment using the compounds of this invention is also recommended as the protective step to assist the patients who are confronting a decrease in oxygen supply to the brain caused by chronic pulmonary diseases with carbon dioxide retention, or following a cardio-pulmonary operation. In the case where transient decreases or cessation of blood supply to the brain is expected during he operation involving the brain, heart or blood vessel, oral or parenteral administration of the protective agents of this invention for a designed period of time prior to the surgery will be effective in making brain cells resistant to anoxia during operation. In this way, accidental cell damage or death of brain cells due to delayed oxygen supply may be avoided.

The protective agents of this invention may be also useful for early treatment or prevention of injury of miners, construction workers or soldiers who may be accidentally exposed to hypoxia or anoxia, by administering agents of this invention regularly, for a certain period of time prior to the engagement of dangerous work, or post exposure.

The compounds of the current invention are similarly useful for protection of tissues other than nervous tissue. Such other tissues as myocardium, for instance, may be irreversibly damaged when myocardial ischemia takes place and cardiac muscle cells become irreversibly damaged during ischemia due to lactic acidosis. However, the main aim is to avoid hyposystole of cardiac muscle brought upon by decrease of mycoplasmal troponin affinity to $Ca^{2+}$ during the period of pH lowering. The protective agents according to the invention are thus not only useful in prevention of myocardial ischemia as the target disease but are also effective to maintain the function of cardiac muscle until the proper therapy can be instituted. Specifically, in angina pectoris patients, regular oral administration of the lactic acid protective agent of this invention can assure protection of cardiac muscle. Further, in acute myocardial ischemia, administration of the agents of this invention orally, by coronary injection, or by intravenous drip in combination with percutaneous transluminal coronary angioplasty (PTCA) may be effective in protection of normal cells neighboring to effected myocardial cell.

Compounds of this invention may be formulated in any form acceptable in medicinal chemistry and pharmaceutical sciences.

The following Examples are intended to illustrate the invention. These examples are not to be interpreted to limit the scope of the invention in any way.

EXAMPLE 1

Lactate Levels and pH in the Neuronal Cells

This example illustrates the measurement of pH and lactate concentration by NMR in rat pups.

Aqueous solution of taurine adjusted to pH 7 with sodium hydroxide in the amount of 16 mmole/kg/day was intraperitoneally administered to groups of Sprague-Dawley strain rats immediately after birth for 10 consecutive days. These animals were designated to be the experimental group. Physiological saline was administered to the control group of rats. Each group consisted of 10 animals.

On the last day of the administration, i.e. at day 10, the animals were each fixed in a special chamber set within a 4.7 T nuclear magnetic resonance apparatus. The normal atmosphere was replaced by pure nitrogen for 7.5 minutes. In this way, anoxia was induced in these animals.

The pH level and the lactate concentration in the cerebral cells before and after anoxia were measured by nuclear magnetic resonance spectroscopy using the procedure described above. Immediately thereafter, the brains were extracted, and the intracerebral taurine levels were quantitatively determined in the perchloric acid extraction fraction obtained from the extracted brains according to procedure described in Example 2.

The taurine amount (as expressed by the taurine/choline ratio) in the experimental group was 1.16 0.06, and in the control group was 0.85+0.05. There was a significant difference ($p<0.005$, t-test) observed between the two groups. This experiment demonstrated that the administration of taurine to the newborn rats immediately after birth produces a significant elevation of the intracerebral taurine concentration.

The lactic acid amount, expressed by the lactic acid/N-acetyl aspartate ratio, was about 0.7 before anoxia and about 2.4 after anoxia, in both the experimental and the control groups. The increase of the lactic acid amount was caused by the production of glucose via anaerobic glycolysis in response to anoxia. The increase was not significantly different between experimental and control groups.

With respect to pH, a significant difference was observed between both groups. The pH value before anoxia was the same, of about pH 7.3, in both groups. In the experimental group, immediately after anoxia the pH dropped to pH 7.0 and to pH 6.85 in the control group. While the pH 7.0 is physiologically acceptable, pH 6.85 is borderline and would most probably result in irreversible damage to the brain cells, if not immediately treated.

EXAMPLE 2

In Vitro Taurine Assay

This example illustrates in vitro NMR method used for measurement and determination of taurine levels.

Taurine levels were determined in rat pups brains perchloric acid (PCA) extracts using high resolution proton spectroscopy. Pups were sacrificed immediately after completion of the study described in Example 1 by exsanguination under pentobarbital anesthesia. Brains were removed and fixed in liquid nitrogen. The frozen brains were pulverized in a liquid nitrogen cooled mortar and pestle and mixed with 4 volumes of 0.5N powdered frozen PCA. The powder mixture was centrifuged in liquid nitrogen cooled centrifuge at 16,000 rpm at $-4°$ C. for 30 minutes. The supernatant was removed and titrated to a pH of 9.0–9.5 by the addition of potassium bicarbonate. The solution was stored in an ice bath for 15 minutes and the potassium perchlorate precipitate was removed by centrifugation at 16,000 rpm at $-4°$ C. The sample was then lyophilized.

A Nicolet NMR System NM-500 (11.75T) was used for high resolution proton spectroscopy. Brain extracts were dissolved in 1 ml of heavy water and placed in a 5 mm NMR tube. Proton spectra were obtained using a one pulse sequence (recycle time 5.7 sec., flip angle 60°) with a spectral width of 6 k into 16 k memory blocks. The Lorentzian corrected height of the center resonance of the C-2 taurine triplet (3.43 ppm referred to trimethylsilyl propionic acid) and choline was used to obtain relative taurine levels. *Magn. Reson. Med.*, 12:172 (1989).

EXAMPLE 3

Guanidinoethane Sulfate Enhances Survival Rate of Mice Exposed to Anoxia

This example illustrates the protective effect of guanidinoethane sulfate against anoxia in adult mice.

GES was prepared according to method described in *J. Pharm. Ext. Ther.*, 211:466 (1979). Taurine and methyl isothiopseudourea were purchased from Sigma, St. Louis, Mo.

Sixty g of taurine were mixed with 100 g of methyl isothiopseudourea in concentrated ammonium hydroxide (120 ml) under a chemical hood. The mixture was heated to 60° C. and maintained at this temperature until evolution of gas ceased. The solution was cooled on ice until crystals were formed. Following the filtration, the crystals were dissolved in a minimum of distilled water and were recrystallized three times from water. Purity of GES was confirmed by proton NMR spectroscopy at 500 MHz (GE Omega-500). The pKa value of the amino moiety of GES was determined to be 12.48

Adult Swiss mice (BK-1 males, 20 g) purchased from Bantin & Kingman, Fremont, Calif. were used. Each batch consisted of 10 mice. Within each batch five mice were selected randomly as experimental animals and the remaining five as controls. Experimental mice received daily intraperitoneal injections of 0.25 ml of GES (50 mg/ml) for 14 days. Control mice received either taurine (50 mg/ml) or sham injections of 0.25 ml of normal saline for 14 days.

At day 14, all mice within the same batch (5 experimental and 5 each of the two control groups) were placed in a specially designed chamber (26.5×24.5×21.0 cm). Anoxia/hypoxia was produced by infusion of pure nitrogen gas (14 ml/min) into the chamber for 2.5 or 2.75 minutes. Anoxia/hypoxia was reversed immediately after these intervals by removing the chamber and placing the mice in a room air environment.

Under this experimental setting, the $LD_{50}$ of anoxia/hypoxia duration is 2.5 min while 2.75 minutes is universally fatal for normal adult mice. Accordingly, two experimental settings, 2.5 and 2.75 minutes of anoxia/hypoxia duration, were chosen to determine the survival rate of GES, taurine and saline treated animals. The results are shown in FIG. 1 and discussed in detail above. Shortly, after 2.75 minutes of exposure, the experimental GES group showed a mortality of only 20%, while both control groups reached a mortality of 100%.

From the above results it is evident that sodium guanidinoethane sulfate can effectively prevent lactic acidosis caused by complete oxygen deficiency.

EXAMPLE 4

Effect of Guanidinoethane Sulfate Against in Vivo Intracellular Acidosis

Using the same experimental procedure as in Example 3, in vivo pH buffering property of guanidinoethanesulfonic acid against the in vivo intracellular acidosis and pH depression caused by anoxia was evaluated.

Aqueous solution of guanidinoethanesulfonic acid (0.3M) was administered daily intraperitoneally to five mice at a dose of 3.75 mmole/kg/day for a period of 14 days. The same number of control mice (5) received intraperitoneal administration of physiological saline solution at a dose of 0.25 ml/animal/day for the same period (14 days).

After the 14 days of administration period of GES or saline, animals were placed in a chamber filled with pure 100% nitrogen for 2 minutes to produce the anoxia state. The pH of the brain was measured in vivo before and after the anoxia by the technique of $^{31}$P spectroscopy using Omega-7 Tesla Magnetic Resonance Spectrophotometer.

The average brain pH values before the anoxia were 7.16±0.04 and 7.11±0.01 for the guanidinoethane sulfate treated animals and for control animals, respectively. No significant difference in pH was observed between these two animal groups before the anoxia. On the other hand, the brain pH values after the anoxia were 7.05±0.05 and 6.90±0.04, for the guanidinoethane sulfate treated animals and for control animals, respectively.

Above findings clearly indicate that guanidinoethane sulfate effectively protects the brain cell from the acidosis damage, and against pH depression under the condition of anoxia, and in this way prevent the brain cells damage caused by lactic acidosis.

EXAMPLE 5

Effect of Taurine on Levels of Lactate, pH and on Brain Resistance to Fasting

This example illustrates the effect of taurine on the levels of lactate, on the tissue pH and on brain resistance to acidosis following fasting.

Sprague-Dawley female rats 14–20 weeks old were mated to stud rats. Insemination was confirmed by the presence of sperm on vaginal smear to determine the due date and to ascertain age at delivery. Pregnant rats were fed laboratory chow ad libitum and allowed free access to water. Pups were born naturally. Individual litters contained 10–15 pups. Smaller litters were excluded.

An equal number of pups from the same dam were divided into three groups: control groups, taurine group, and fasting group. Each group contained 10 pups. Taurine pups received intraperitoneal injection of taurine (Sigma, St. Louis), 2 mg/g (water solution neutralized to pH 7 with a NaOH), daily, starting day 2 postnatally. The control fasting pups received sham injections according to the same protocol. Fasting pups were removed from the dam 48 hours prior to the experiments and were kept in a separate cage where their body temperature was kept normal by warming blanket. Pups were studied on day 10 postnatally.

A Nicolet NMR System NT-200 (4.7T) was used. Each pup was anesthetized with ketamine, 50 mg/kg. Pups were held in a specially designed padded holder which was placed in the probe chamber which contained a one turnaround surface coil (10 mm diameter) tunable to the resonance frequency of proton and $^{31}$P. The pup holder was positioned such that the surface coil was centered over the pup calvarium. To avoid signal contamination, scalp and temporal muscle were retracted. To produce anoxia, 100% nitrogen gas rapidly infused in amount of 14 l/min into the chamber. Anoxia was reversible by infusion of air. Calibration studies using an oxygen meter (OM-1 Biological Oxygen Meter, Microelectrodes, Inc.) confirmed that this technique produced complete $O_2$ depletion in the chamber or its reversal within one minute. The temperature of the chamber was kept at 32°–33° C. by warmed air throughout the studies and monitored with a flexible nonmagnetic thermometer (YSI Series 402, Yellow Spring Instrument Co.). Field homogeneity was maximized by skimming on tissue water proton signals. $_{31}$P spectra were obtained using a one pulse sequence at 80.99 MHz with a spectral width of 6K into 4K memory blocks (recycle time 2.7 sec.).

Previous studies under identical experimental settings indicated that contribution by substrates other than lactate to the resonance at 1.32 ppm is negligible in anoxia experiments on rat pups in the early postnatal stage. This is probably due to the lack of fatty acid release in response to anoxia in the early neonate brain.

For confirmation, calibration studies were performed on nine animals (three in each group) using a lactate editing method as follows. Proton signals were obtained during a two acquisition mode in a single sequence where the first acquisition is for a 1331-τ-2662 and the second for 1331-τ-hard 180° pulse. Signals were stored in alternate mode into two different memory blocks (4 k each). Total recycle time as 2.7 seconds with identical predelay time for each half. The interpulse delay of the Hore sequence was adjusted such that the lactate resonance observed least attenuation. 90 free induction decays (FIDs) were accumulated for each memory block. Signals stored in each memory block were processed separately, yielding proton spectra with a lactate resonance with and without 180° phase modulation acquired essentially at identical times. An edited lactate spectrum was obtained by subtracting the two spectra. The calibration studies confirmed that no substrate other than lactate contributed to the intensity of the resonance detected at 1.32 ppm significantly under these experimental settings in the 10 day old neonate. Accordingly, proton spectra for this study were obtained using a 1331-τ-2662 pulse with a delay of 68 ms (spectral width: 2 KHz, memory block: 4 k, recycle time 2.7 seconds).

The sum of 180 FIDs was blocked (7.5 minutes). Each animal was subjected to 7.5 minutes of total anoxia, and proton spectra were obtained every 7.5 minutes starting 15 minutes before the anoxic period and for 45 minutes thereafter (total of 10 blocks). The broad resonance with short $T_2$ was removed using the convolution difference technique. The FID-like signals from the remaining water proton signals were eliminated by applying nine function anodization. Line broadening of 35 Hz or 5 Hz was applied as noise filter for $_{31}$P or proton spectra, respectively. Lorentzian corrected heights were used for quantification. For $^{31}$P data, the relative levels of each substrate were expressed as the ratio of the levels of each substrate to total phosphorus levels. Relative lactate levels were expressed as the ratio of lactate levels to N-acetyl-aspartate (NAA). Intracellular pH was estimated using the equation: pH-6.77+log (δ-3.29)/(5.68-δ), where δ is the chemical shift of Pi referred to that of phosphocreatine (PCr). Blood glucose levels after a period of 7.5 minutes of anoxia were determined using Chemstrip bG (Boehringer-Mannheim).

EXAMPLE 6

Alkaline Shifter Effect of Guanidinoethane Sulfate on Delayed Neuronal Death of CA1 Neurons This example illustrates the protective effect of guanidinoethane sulfate, as an alkaline shifter, on delayed neuronal death of CA1 neurons in adult male gerbils.

Determination GES Levels in the Gerbil Brain

Guanidinoethane sulfate (GES) was prepared as described in *Arch. Biochem. Biophs.*, 210:698 (1981). Taurine and methyl isothiopseudourea were purchased from Sigma (St. Louis, Mo.).

Sixty g of taurine was mixed with 100 g of methyl isothiopseudourea in concentrated ammonium hydroxide (120 ml) under a chemical hood. The mixture was heated to 60° C. and maintained at this temperature until evolution of gas ceased. The solution was cooled on ice to crystalize GES, and filtered. The crystals were dissolved in a minimal amount of distilled water and then recrystallized three times from water. The purity of GES was confirmed by proton NMR spectroscopy at 500 MHz (GE Omega-500).

Adult male gerbils (ca. 70 g) were divided into three groups of 5 gerbils each. Control group received saline and experimental group received GES. Taurine group served as an additional control. The GES group received daily injections of 0.25 ml (625 mg/kg), GES or taurine (dissolved in distilled water and neutralized to pH=7.4 with 1N NaOH), intraperitoneally for two weeks. The saline group received 0.25 ml of saline injections.

After two weeks, animals were sacrificed by exsanguination under pentobarbital anesthesia. Brains were removed and fixed in liquid nitrogen. The frozen brains were pulverized in a liquid nitrogen cooled mortar and pestle, and mixed with 4 volumes of 0.5N powdered frozen perchloric acid. The powder mixture was centrifuged in liquid nitrogen cooled centrifuge tubes at 16,000 rpm at –4° C. for 30 minutes. The supernatant was removed and titrated to a pH of 9.0–9.5 by the addition of potassium bicarbonate. The solution was stored in an ice bath for 15 minutes and the potassium perchlorate precipitate was removed by centrifugation at 16,000 rpm at –4° C.

Aliquots (0.5 ml) of the extracts obtained above were placed on a dual bed ion exchange column containing 6×0.5 cm Dowex AG1 anion exchange resin (chloride form) layered over 6×0.5 cm Dowex AG50 cation exchange resin (hydrogen form). Water (3 ml) then added to the column. The eluent, guanidinoethyl sulfonate, was free from other naturally occurring guanidino compounds, such as arginine. The color reagent was 5% w/v naphthol in ethanol containing 2.5% of 1% aqueous diacetyl solution. Aliquots of eluent were taken and diluted to 0.7 ml with water. Sodium hydroxide (3N;0.1 ml) was added, followed by 0.2 ml of the color reagent. After 18 min., absorbance was read at 545 nm using a Gilford Spectrophotometer to determine brain GES level. Results are shown in Table 1.

TABLE 1

Brain GES Level (μmg Wet Weight)

Controls (5) 0.36±0.13

GES Group (5) 2.73±0.36

The brain GES level for the saline group was 0.36 μM/g ±0.13 while that for the GES group was about 7 times higher 2.73 μ.M/g±0.36.

Determination of Intracellular Alkali Shift

Intracellular pH measurement of gerbil brain was performed non-invasively using $^{31}P$ nuclear magnetic resonance (NMR) in vivo spectroscopy. AGE Omega CSI-7T (useful bore 120 mm, horizontal, 7T) was used.

Gerbils were divided into two groups of 7 animals each. Control group received saline. Saline ischemia group received saline. GES group received GES. Gerbils were anesthetized with pentobarbital, 50 mg/kg. Gerbils were held in a padded holder which was placed in the probe chamber containing a one turn round surface coil (5 mm diameter) tunable to the resonance frequency of proton and $^{31}P$. To avoid signal contamination, the scalp and temporal muscle were retracted. The body temperature was kept at 37° C. using a non-magnetic heating pad. Field homogeneity was maximized by skimming on tissue water proton signals. $^{31}P$ spectra were obtained using a one pulse sequence at 121.67 MHz with a spectral width of 10K and stored into 4K memory blocks (recycle time 2.7 sec). The broad resonance with short $T_2$ on $^{31}P$ spectra was removed by the convolution difference technique. Line broadening of 30 Hz was applied as noise filter. Intracellular pH was estimated using the equation: $pH=6.77+\log\{(\delta-3.29)/(5.68-\delta)\}$, where $\delta$ is the chemical shift of inorganic phosphate (Pi) referred to that of phosphocreatine (PCr).

Representative $^{31}P$ spectra of gerbil brain utilized for the pH determination are shown in FIG. 9.

TABLE 2

Intracellular pH of Gerbil Brain

Saline Group (n=7) 7.17±0.06

GES Group (n=7) 7.25±0.07, mean and standard deviation. *p<0.05 (t-test)

Alkali shift by GES is clearly proven from the results. The intracellular pH for the saline group was 7.17, while that for the GES group was 7.25.

Consequently, administration and presence of GES in the brain clearly shifts pH from lower level 7.17 to higher level 7.25.

Effect GES Ischemia on Neuronal Density in CA1 Regions

The gerbil forebrain ischemia model of Kirino (REFERENCE, please) was employed as follows.

Animals were divided into 4 groups. Two groups of 5 animals each served as control.

First control group was administered daily for fourteen days 0.25 ml of saline. No ischemia was induced.

Second control group was administered 0.25 ml of 625 mg/kg of GES daily for fourteen days. No ischemia was induced.

Third group of ten animals was control ischemia group. This group was administered with 0.25 ml of saline daily for 14 days. Then, the ischemia was induced.

Fourth group of 16 animals was administered 0.25 ml of 625 mg/kg of GES for 14 days, followed by induced ischemia.

Animals were anesthetized with 1% halothane, 70% nitrous oxide, and 29% oxygen. The subscalp and rectal temperature were monitored and kept constant at 37° C. using a controlled heating system starting 30 minutes prior to one hour after induction of ischemia. Ischemia in experimental groups (saline and GES ischemia groups) was induced by occlusion of the carotid arteries bilaterally for 5 minutes using small aneurysm clips. Animals in the two control groups (saline and GES controls) received sham surgery but no ischemia was induced.

Seven days after induced ischemia and recirculation, animals were perfused transcardially with 50 cc of normal saline followed by 500 cc of 5% paraformaldehyde in 0.1M phosphate buffer (pH=7.3), at 100 cm $H_2O$, under deep pentobarbital anesthesia. Brains were removed and fixed in the same buffered paraformaldehyde solution for 14 days. Sections (6 µm thick) containing the dorsal hippocampus at the level 1.4–1.7 mm posterior to the bregma were prepared on a cryostat from paraffin embedded brain. Sections were stained with hematoxylin and eosin and examined in a double blinded fashion. The number of viable neurons within the CA1 region was counted using an Olympus BH-2 microscope at ×400. The results represents the average of the counts.

Representative photomicrographs for control, saline ischemia and GES ischemia groups are provided in FIG. 10.

FIG. 10 shows the representative photomicrographs for control (left panel A) saline with induced ischemia (middle panel B) and GES with induced ischemia (right panel C).

The Table 3 summarizes the counts per mm of neuronal density in CA1 region.

Significantly higher neuronal density was observed in the GES ischemia than saline ischemia group as seen in Table 3 and also as seen in FIG. 10 where the neuronal density of the brain of the animals treated with GES alkaline shifter is clearly seen.

TABLE 3

Neuronal Density in CA1 Region (/nm)

Saline Control Group (n=5) 255.1±11.7§

GES Control Group (n=5) 249.0±9.4§

Saline Ischemia Group (n=10) 17.75±12.73*

GES Ischemia Group (n=16) 61.1±55.11* mean and standard division, §NS, *p<0.05 (t-test)

The CA1 neuronal density in the saline control group was 255.1/mm±9.4. In the saline ischemia group density was 17.75±12.73 and in the GES ischemia group 61.1±55.11 there was a significant difference (p<0.05, t-test) observed between the two groups. GES treatment preceding ischemia has shown to have four times higher protective activity as measured by the neuronal density in CA1 region.

Behavioral Animal Studies of Neuronal Activity After Ischemia

Ischemia was induced as described above. Motor activity was analyzed using a PC driven automatic behavior analyzer as follows. Animals were placed individually in automated motor activity chambers (Omnitech Digiscan, Columbus, Ohio). A horizontally aligned array of either infrared beams on each side of the chamber (39×39×39 cm high), located 2.5 cm above the floor and 2.5 cm apart, detected animals movements. Previous studies indicated that "distance traveled" (m/hr) provide the most reliable parameter for study of neuronal activity. Animals were studied prior to and 1, 2, 3, 7 day after induction of ischemia. Motor activity was monitored for 6 hours between 11:00 pm and 5:00 am.

FIG. 12 summarizes the result. Post-ischemia hyperactivity consistently seen in the saline group was significantly suppressed in the GES group.

As seen from FIG. 11, before ischemia animals submitted to treatment with GES travelled approximately 150 m/hours while both controls shorter travelling distance. Following ischemia, however, control ischemia group showed post-ischemic hyperactivity from the first day after the ischemia when the travelling distance in the ischemia control reached about 235 m/hours which was more than 2.5 times of the traveling distance of the GES ischemia group. GES ischemia group was able to suppress post-ischemic hyperactivity to close to normal levels of the non-ischemia control group.

EXAMPLE 7

Alkaline Shift Effect of Guanidinoethane Sulfate in Reducing the Level of Lactic Acidosis in Mice Exposed to Anoxia This example illustrates the shift in intracellular pH, to a more alkaline level, for GES treated mice exposed to anoxia.

Adult Swiss mice (BK-1 male 20 g) purchased from Bantin & Kingman, Fremont, Calif., were used. Each batch consisted of 15 mice. Within each batch, five mice were selected randomly to be in the GES, taurine, or control group. A taurine group was included to serve as additional control. Since taurine does not cross the blood brain barrier freely in the adult mouse, taurine supplementation does not significantly alter brain taurine levels. Taurine supplementation, however, does increase systemic taurine levels. The GES or taurine group received daily injections of GES or taurine (dissolved in distilled water and neutralized to pH=7.4 with 1N NaOH), 0.25 ml (625 mg/kh), intraperitoneally for two weeks, while controls received sham injections (normal saline).

GES was prepared as described above. Taurine and methyl isothiopseudourea were purchased from Sigma (St. Louis, Mo.). Sixty g of taurine was mixed with 100 g of methyl isothiopseudourea in concentrated ammonium hydroxide (120 ml) under a chemical hood. The mixture was heated to 60° C. and maintained at this temperature until evolution of gas ceased. The solution was cooled on ice to crystalize GES, and filtered. The crystals were dissolved in a minimal amount of distilled water and then recrystallized three times from water. The purity of GES was confirmed by proton NMR spectroscopy at 500 MHz (GE Omega-500). The pKa value of the amidino moiety of GES was determined to be 12.48.

A GE Omega CSI-7T (clear bore 120 mm, horizontal, 7T) was used. Mice were anesthetized with pentobarbital, 50 mg/kg, intraperitoneally. Mice were held in a padded holder which was placed in the probe chamber containing a one turn round surface coil (5 mm diameter) tunable to the resonance frequency of proton and $^{31}P$. To avoid signal contamination, the scalp and temporal muscle were retracted. The animal body temperature was kept at 37° C. using a non-magnetic heating pad. Field homogeneity was maximized by skimming on tissue water proton signals. $^{31}P$ spectra were obtained using a one pulse sequence at 121.67 MHz with a spectral width of 10K and stored into 4K memory blocks (recycle time 1.2 sec). Every 100 transients (2 minutes) were blocked. In order to obtain higher accuracy, preanoxia steady state pH was determined using block average files of three blocks (300 transients, 6 minutes). Anoxia was then introduced by infusion of 100% $N_2$ into the chamber (14 L/min). The first blocks (100 transients, 2 minutes) immediately after $N_2$ introduction were utilized for post anoxia pH measurement. The broad resonance with short $T_2$ on $^{31}P$ spectra was removed by using the convolution difference technique. Line broadening of 30 Hz was applied as noise filter. Intracellular pH was estimated using the equation: pH=6.77+log{(δ−3.29)/5.68—δ)}, where δ is the chemical shift of inorganic phosphate (Pi) referred to that of phosphocreatine (PCr). The intracellular and pH values demonstrating alkaline shift for GES treated mice, are shown in FIG. 12.

Arterial blood gas sample was collected by puncture of the lower portion of the descending aorta under pentobarbital anesthesia. Analysis was performed on a Corning 168 Blood Gas Analyzer.

Animals were sacrificed by exsanguination under pentobarbital anesthesia. Brains were removed and fixed in liquid nitrogen. The frozen brain was pulverized in a liquid nitrogen cooled mortar and pestle, and mixed with powdered frozen perchloric acid, 0.5N, 4 volumes. The powder mixture was centrifuged in liquid nitrogen cooled centrifuge tubes a 16,000 rpm at −4° C. for 30 minutes. The supernatant was removed and titrated to a pH of 9.0–9.5 by the addition of potassium bicarbonate. The solution was stored in an ice bath for 15 minutes and the potassium perchlorate precipitate was removed by centrifugation at 16,000 rpm at −4° C.

Aliquots (0.5 ml) of the extracts obtained above were placed on a dual bed ion exchange column containing 6×0.5 cm of Dowex AG1 anion exchange resin (chloride form) layered over 6×0.5 cm of Dowex Ag50 cation exchange resin (hydrogen form). Water (3 ml) was then added to the column to collect the eluent, guanidinoethane sulfonate, free from other, naturally occurring guanidino compounds, such as arginine. The color reagent was 5% w/v naphthol in ethanol containing 2.5% of 1% aqueous diacetyl solution. Aliquots of eluent were taken and diluted to 0.7 ml with water. Sodium hydroxide (3N; 0.1 ml) was added followed by 0.2 ml of the color reagent. After 18 min, absorbance was read at 545 nm using a Gilford Spectrophotometer.

A Varian LC 5000 HPLC system with Gilson Microfractionator and EM ScienceLiChrospher column (SI 100 RP-8, 10 micron, 10 mm×25 cm) was used. An aliquot of the extract prepared as above, ca. 2 ml, was passed through a cation-exchange column (Bio-Rad Laboratories, AG 50W-X8, 200–400 mesh H$^+$form, 5×15 mm) and washed three times with 1 ml of distilled water. The effluent and washings were combined (final volume ca. 5 ml). The washings are necessary to eliminate interfering substances and help protect the column from contamination caused by too much absorption of other amino acids. Taurine was labelled with dansyl chloride (DNS-Cl) as follows. Taurine sample, 0.2 ml, was combined with DNS-Cl, 0.2 ml, and heated in the water bath at 40° C. for ten minutes to complete the labelling reaction. 10 μl of the sample was injected into the column and eluted at a flow rate of 0.5 ml/min with a mobile phase of methanol:water (3:65 v/v), 0.6% acetic acid and 0.008% triethylamine. Taurine concentration was determined at an absorbance of 254 nm.

Brain lactate levels were determined for mice exposed to 2.5 minutes of anoxia as follows. Animals were exposed to 2.5 minutes of anoxia under pentobarbital anesthesia. Immediately after the exposure, animals were immersed into a liquid nitrogen. The frozen brains were removed by chiseling and extracted as described above. Lactate concentration was determined using the lactate dehydrogenase reaction.

Animals which received GES or taurine supplementation did not show any observable adverse effects in their behavior or respiratory pattern. FIG. 13 31P spectra of mice brain. A mice brain pH of pre- and post (2 minutes) anoxia are shown in FIG. 12. High GES levels significantly increased brain intracellular pH (alkaline shift), while arterial blood gas parameters including pH remained essentially unchanged. With anoxia, brain pH became more acidic in all three groups. However, brain pH of the GES group remained higher, retaining the degree of alkaline shift. Lactate levels post 2.5 min anoxia were essentially identical among the three groups demonstrating that there was no significant difference in activities of anaerobic glycolysis among the three groups. Results are shown in Table 4.

TABLE 4

| | In vitro Parameters | | |
|---|---|---|---|
| | Control (n = 5) | GES (n = 5) | Taurine (n = 5) |
| GES (mM) | | | |
| Taurine (mM) | | | |
| pH | 7.28 ± 0.02* | 7.29 ± 0.03 | 7.26 ± 0.04 |
| pO$_2$ (mmHg) | 95.6 ± 12.2 | 98.0 ± 5.8 | 97.7 ± 12.9 |
| pCO$_2$ (mmHg) | 44.5 ± 2.67 | 41.0 ± 5.49 | 41.26 ± 5.39 |
| Lactate (mM) | 0.50 ± 0.07 | 0.50 ± 0.07 | 0.48 ± 0.08 |

What is claimed is:

1. A method for treatment of Alzheimer disease caused by abnormal β-amyloid peptide metabolism resulting from intracellular acidosis or a pH fluctuation between the normal pH 7.3 and acidic intracellular pH between pH 5.0 and 7.0, said method comprising the step of administering to a subject in need of such treatment a pharmaceutically effective amount of an alkaline shifter compound or a buffering compound, wherein said compound is able to shift the intracellular pH of the cell from acidic pH below 7.0 to physiologically acceptable pH of about 7.1 to 7.4; and wherein said compound crosses the blood-brain-barrier, is permeable through a cell membrane, is able to decrease hydrogen ion concentration and has pKa from about 6.8 to about 11.4.

2. A method for prevention of development and reversal of formation of senile plagues and neurofibrillary fibers caused by abnormal β-amyloid peptide metabolism resulting from intracellular acidosis or a pH fluctuation between the normal pH 7.3 and acidic intracellular pH from about pH 5.0 to about pH 7.0, said method comprising a step of administering to a subject in need of such treatment a pharmaceutically effective amount of an alkaline shifter compound or a buffering compound, wherein said compound is able to shift the intracellular pH of the cell from acidic pH below 7.0 to physiologically acceptable pH of about 7.0 to 7.4; and wherein said compound crosses the blood-brain-barrier, is permeable through a cell membrane, is able to decrease hydrogen ion concentration and has pKa from about 6.8 to about 11.4.

3. The method of claim 2, wherein the protective effect of the compound is achieved by decreasing the acidifying effect of protons of intracellular lactic acid generated by anaerobic glycolysis.

4. The method of claim 3 wherein the alkaline shifter compound is selected from the group consisting of guanidinoethane sulfate, guanidinoethane sulfonic acid, 3-(n-morpholino) propanesulfonic acid, N-2-hydroxyethyl-piperazine-N'-ethanesulfonic acid, and N-2-hydroxyethyl-piperazine-N'-propanesulfonic acid.

5. The method of claim 4 wherein the compound is the alkaline shifter compound having a pKa value from about 8.4 to about 11.

6. The method of claim 5 wherein the compound is the buffering compound having a pKa value from about 6.8 to about 8.41.

7. The method of claim 5, wherein the compound is guanidinoethane sulfate.

8. The method of claim 5, wherein the compound is guanidinoethane sulfonic acid.

9. A method for prevention of development and reversal of formation of senile plaques or neurofibrillary tangles resulting from abnormal β-amyloid peptide metabolism following a shift in intracellular pH toward acidosis, said pH shifting from about pH 7.3 to pH between 7.0 to about 5.0, said acidosis causing said β-amyloid peptide to aggregate into senile plaques or neurofibrillary tangles, said method comprising a step of administering to a subject in need of such treatment a pharmaceutically effective amount of an alkaline shifter compound or a buffering compound selected from the group consisting of taurine, guanidinoethane sulfate, guanidioethane sulfonic acid, 3-(n-morpholino) propanesulfonic acid, N-2-hydroxyethyl-piperaxine-N'-ethanesulfonic acid, and N-2-hydroxyethylpiperazine-N'-propanesulfonic acid, wherein said compound is able to shift the intracellular pH of the cell from acidic pH below 7.0 to pH of about 7.0 to 7.4; and wherein said compound crosses blood-brain-barrier, is permeable through a cell membrane and is able to decrease hydrogen ion concentration.

* * * * *